United States Patent [19]

Sinclair

[11] Patent Number: 5,180,765
[45] Date of Patent: Jan. 19, 1993

[54] BIODEGRADABLE PACKAGING THERMOPLASTICS FROM LACTIDES

[75] Inventor: Richard G. Sinclair, Columbus, Ohio

[73] Assignee: BioPak Technology, Ltd., Golden, Colo.

[21] Appl. No.: 579,005

[22] Filed: Sep. 6, 1990

Related U.S. Application Data

[63] Continuation-in-part of Ser. No. 387,678, Jul. 31, 1989, abandoned, which is a continuation-in-part of Ser. No. 229,896, Aug. 8, 1988, abandoned.

[51] Int. Cl.$^5$ ............................................. C08K 5/10
[52] U.S. Cl. ...................................... 524/306; 524/310; 524/315; 524/317; 524/320; 528/354; 528/361; 523/124
[58] Field of Search ............... 524/306, 310, 315, 317, 524/320; 528/354, 361; 523/124

[56] References Cited

U.S. PATENT DOCUMENTS

| | | | |
|---|---|---|---|
| 1,995,970 | 3/1935 | Dorough | 260/2 |
| 2,396,994 | 3/1946 | Filachione et al. | 260/484 |
| 2,438,208 | 3/1948 | Filachione et al. | 260/78.3 |
| 2,703,316 | 3/1955 | Schneider | 260/78.3 |
| 2,758,987 | 8/1956 | Salzberg | 260/78.3 |
| 2,951,828 | 9/1960 | Zeile et al. | 260/77.5 |
| 3,268,487 | 8/1966 | Klootwijk | 260/78.3 |
| 3,531,561 | 9/1970 | Trehu | 264/210 |
| 3,565,869 | 2/1971 | De Prospero | 528/361 |
| 3,636,956 | 1/1972 | Schneider | 128/335.5 |
| 3,755,558 | 8/1973 | Scribner | 424/47 |
| 3,773,919 | 11/1973 | Boswell et al. | 424/19 |
| 3,982,543 | 9/1976 | Schmitt et al. | 128/335.5 |
| 4,137,921 | 2/1979 | Okuzumi et al. | 128/335.5 |
| 4,279,249 | 7/1981 | Vert et al. | 128/92 D |
| 4,534,349 | 8/1985 | Barrows | 128/334 R |
| 4,539,981 | 9/1985 | Tunc | 128/92 B |
| 4,603,695 | 8/1986 | Ikada et al. | 128/334 R |
| 4,683,288 | 7/1987 | Tanaka et al. | 528/361 |
| 4,719,246 | 1/1988 | Murdoch et al. | 521/134 |
| 4,728,721 | 3/1988 | Yamamoto et al. | 528/361 |
| 4,789,726 | 12/1988 | Hutchinson | 528/354 |
| 4,797,468 | 1/1989 | De Vries | 528/354 |
| 4,898,186 | 2/1990 | Ikada et al. | 606/62 |
| 5,076,983 | 12/1991 | Loomis et al. | 264/101 |

FOREIGN PATENT DOCUMENTS

| | | |
|---|---|---|
| 808731 | 3/1969 | Canada . |
| 923245 | 3/1973 | Canada . |
| 58481 | 8/1982 | European Pat. Off. . |
| 311065 | 4/1989 | European Pat. Off. . |
| 314245 | 5/1989 | European Pat. Off. . |
| 316992 | 5/1989 | European Pat. Off. . |
| 321176 | 6/1989 | European Pat. Off. . |
| 368571 | 5/1990 | European Pat. Off. . |
| 946664 | 8/1956 | Fed. Rep. of Germany . |
| 14548 | 8/1958 | Fed. Rep. of Germany . |

(List continued on next page.)

OTHER PUBLICATIONS

"The Effect of the Addition of Low Molecular Weight Poly(DL-Lactide) on Drug Release from Biodegradable Poly(DL-Lactide) Drug Delivery Systems"; Bodmeier et al.; Int. J. Pharmaceutics, 51, 1-8 (1989).

(List continued on next page.)

Primary Examiner—Paul R. Michl
Assistant Examiner—Edward J. Cain
Attorney, Agent, or Firm—Sheridan, Ross & McIntosh

[57] ABSTRACT

Environmentally biodegradable compositions of poly(-lactic acid) plasticized with lactic acid, D-lactide, L-lactide, meso D,L-lactide, racemic D,L-lactide, oligomers of lactic acid, oligomers of lactide, derivatives of oligomers of lactic acid, or various mixtures thereof; the compositions are suitable replacements of thermoplastic polymer compositions; the compositions are useful for pliable films and other packaging applications conventionally served by polyethylene and other nondegradable thermoplastics; homopolymers or copolymers of D-lactic acid, L-lactic acid, D-lactide, L-lactide, meso D,L-lactide, and/or racemic D,L-lactide having properties similar to other known polymers may be prepared by varying the ratios of monomer and polymerization conditions, the amount and type of plasticizer in the polymer and process conditions; additives and subsequent treatment are also used to modify properties.

110 Claims, 5 Drawing Sheets

FOREIGN PATENT DOCUMENTS

| | | |
|---|---|---|
| 1112293 | 8/1961 | Fed. Rep. of Germany . |
| 1153902 | 5/1963 | Fed. Rep. of Germany . |
| 69212 | 5/1969 | Fed. Rep. of Germany . |
| 3820299 | 12/1988 | Fed. Rep. of Germany . |
| 41-17675 | 10/1966 | Japan . |
| 43-2948 | 2/1968 | Japan . |
| 44-15789 | 7/1969 | Japan . |
| 61-36321 | 2/1986 | Japan . |
| 1-225622 | 9/1989 | Japan . |
| 99836 | 12/1961 | Netherlands . |
| 9001521 | 2/1990 | PCT Int'l Appl. . |
| 755447 | 8/1956 | United Kingdom . |
| 779291 | 7/1957 | United Kingdom . |
| 825335 | 12/1959 | United Kingdom . |
| 932382 | 7/1963 | United Kingdom . |
| 1048088 | 11/1966 | United Kingdom . |
| 1593288 | 7/1981 | United Kingdom . |
| 8400303 | 2/1984 | World Int. Prop. O. . |

OTHER PUBLICATIONS

Production and characteristics of high molecular especially optically active polyesters of lactic acid, an investigation of the stereochemistry of macromolecular compounds; Kleine H. H.; Doctoral Dissertation, University of Munich, West Germany; 95 pages, (1957).

Uber hochmolekulare, insbesondere optisch aktive Polyester der Milchsaure, ein Beitrag zur Stereochemie makromolekularer Verbindungen (High Molecular Weight, Especially Optically Active Polyesters of Lactic Acid: An Investigation of the Stereochemistry of Macromolecular Compounds); Kleine and Kleine; Macromolekulare Chemie, vol. 30, pp. 23–38, (1959)–Translation Provided.

Preparation of Some Polyesters by Organometallic-catalyzed Ring Opening Polymerization; Tsuruta, Teiji et al; Makromolekulare Chemie, 75, 1964; pp. 211–214.

Polylactic Acid for Surgical Implants; Kulkarni, R. K. et al; Arch. Surg., vol. 93, Nov. 1966, pp. 839–843.

Some Optically Active Polyesters and Polyamides; Schulz, Rolf; IUPAC International Symposium on Macromolecular Chemistry, Budapest 1969, pp. 185–212.

Biodegradable Poly(lactic acid) Polymers; Kulkarni, R. K. et al; J. Biomed. Mater. Res. vol. 5, 1971, pp. 169–181.

Preparation and Evaluation of Glycolic and Lactic Acid-Based Polymers for Implant Devices Used in Management of Maxillofacial Trauma, I; Sinclair, R. G. et al; Final Scientific Report under Contract No. DADA17-72-C-1053 by Battelle Columbus Laboratories, Columbus, Ohio, supported by U.S. Army Medical Research and Development Command, Washington, D.C. 20314, 1972.

Investigation of the structure of solution grown crystals of lactide copolymers by means of chemical reactions; Fischer, E. W. et al; Kolloid-Z.u.Z. Polymere 251, 1973, pp. 980–990.

Development of a Synthetic Polymer Burn Covering; Gregory, J. B. et al; U.S. Nat. Tech. Inform. Serv., AD Rept. No. 759 381, Mar. 1973.

Biodegradable Polymers for Sustained Drug Delivery; Schindler, A. et al; Contemporary Topics in Polymer Science (Eds. E. M. Pearce et al) Plenum Press, New York, vol. 2 (1977) pp. 255–257.

Polylactide, II, Viscosity-Molecular Weight Relationships and Unperturbed Chain Dimensions; Schindler, A. et al; Journal of Polymer Science: Polymer Chemistry Edition, vol. 17, 1979, pp. 2593–2599.

Stereoregular Bioresorbable Polyesters for Orthopaedic Surgery; Vert, M. et al; Makromol. Chem., Suppl. 5, pp. 30–41, (1981).

Lactic acid polymers: strong, degradable thermoplastics; Wehrenberg II, R. H.; Materials Engineering, Sep. 1981, pp. 63–66.

Biodegradable Composites for Internal Fixation; Christel, P. et al; Adv. Biomaterials, 3, 1982, pp. 271–280.

Medical Editorial-Strong biodegradable thermoplastics; Materials Engineering, (May 1982), p. 56.

Configurational structures of lactic acid stereocopolymers as determined by $^{13}C-\{^{31}H\}$ n.m.r.; Chabot et al; Polymer, vol. 24, (Jan. 1983), pp. 53–59.

Biocompatible Poly-L-Lactide Fibers; Hyon, S. H. et al; ACS Polym. Preprint, vol. 24, No. 1, 1983, pp. 6–7.

Characterization of Poly(D,L-Lactic Acid) by Gel Permeation Chromatography; Van Dijk, J.A.P.P.; Journal of Polymer Science: Polymer Chemistry Edition, vol. 21, 1983, pp. 197–208.

Crystallization kinetics of poly(L-lactic acid); Vasanthakumari; Polymer, Feb. 1983, vol. 24, pp. 175–178.

The Ring Opening Polymerization of D,L-Lactide in the Melt Initiated with Tetraphenyltin; Kohn, F. E. et al; Journal. Appl. Polymer Science, vol. 29, pp. 4265–4277 (1984).

Bioresorbable Plastic Materials for Bone Surgery; Vert, M. et al; Macromolecular Biomaterials, Chapter 6, Editors—Garth W. Hastings and Paul Ducheyne, CRC Press, Inc. Boca Raton, Fla., 1984, pp. 120–142.

(List continued on next page.)

OTHER PUBLICATIONS

Melt Spinning of Poly-L-Lactide and Hydrolysis of the Fiber In Vitro; Hyon, S. H. et al; Polymers as Biomaterials, American Chemical Society: Washington, D.C., 1985, ACS Symp. Ser. pp. 51–65.

Polylactones, 6, Influence of various metal salts on the optical purity of poly(L-lactide); Kricheldorf, H. R.; Polym. Bull. (Berlin), 14(6), 1985, pp. 497–502.

In-Vivo Degradation of Poly(Lactic Acid) of Different Molecular Weights; Chawla, A. S. et al; Biomat., Med. Dev., Art. Org., 13(3&4), pp. 153–162 (1985–86).

Is Lactic Acid a Commodity Chemical?; Lipinsky, E. S. and Sinclair, R. G.; CEP Chemical Engineering Progress, Aug. 1986, pp. 26–32.

Biomedical Polymers from Chiral Lactides and Functional Lactones: Properties and Applications; Vert, M.; Macromol. Chem., Macromol. Symp. 6, pp. 109–122, (1986).

Amorphous and crystalline morphologies in glycolic acid and lactic acid polymers; Cohn, D. et al; Polymer, vol. 28, Nov. 1987, pp. 2018–2022.

In vivo Untersuchungen der Festigkeitseigenschaften biologisch abbaubarer Polymere zur Anwendung als Osteosynthesematerialien (In vivo tests of the stability of biodegradable polymers for use as osteosynthesis materials); Gerlach, K. L. et al; Dtsch Z Mund Kiefer Gesichtscher; 11; 1987; pp. 211–216—Translation Provided.

Characterization of Polylactide Synthesis; Jamshidi, K. et al; Polym. Prepr. (Am. Chem. Soc., Div. Polym. Chem.) 28(1), 1987, pp. 236–237.

Polylactones, 13, Transesterification of Poly(L-Lactide) with Poly(Glycolide), Poly($\beta$-Propiolactone), and Poly($\epsilon$-Caprolactone); Kricheldorf, H. R. et al; J. Macromol. Sci.-Chem., A24(11), 1987, pp. 1345–1356.

Synthesis of high-molecular-weight poly(L-lactide) initiated with tin 2-ethylhexanoate[a]); Leenslag, Jan et al; Makromol. Chem. 188, (1987) pp. 1809–1814.

Lactic Acid Polymers-Controlled Release Applications for Biomedical Use and Pesticide Delivery; Sinclair, R. G.; Proceedings of the First Annual Corn Utilization Conference, Jun. 11–12, 1987, pp. 221–236.

Formation of Poly(lactide) with Controlled Molecular Weight, Polymerization of Lactide by Aluminum Porphyrin; Trofimoff, S. et al; Chem. Lett. 1987, pp. 991–994.

Body Absorbable Osteosynthesis Devices; Tunc, D. C. et al; Advances in Biomedical Polymers, Edited by Charles G. Gebelein, Plenum Press, New York and London, 1987, pp. 87–99.

Vergleichende Untersuchungen uber die Dauerschwingfestigkeit absorbierbarer Polymere in der Mund- und Kieferchirurgie (Comparative Studies of the Long-Term Vibration Resistence of Absorbable Polymers in Oral (Mouth and Jaw) Surgery); Gerlach, K. L. et al Dtsch. Zahnaerztl. Z., 43, 1988, pp. 376–378—Translation Provided.

Thermal characterization of polylactides; Jamshidi, K. et al; Polymer, vol. 29, (Dec. 1988) pp. 2229–2234.

Poly(Lactones), 9, Polymerization Mechanism of Metal Alkoxide Initiated Polymerizations of Lactide and Various Lactones; Kricheldorf, H. R. et al; Macromolecules, 21, 1988, pp. 286–293.

Boehringer Ingelheim KG, Chemical Division, D-6507 Ingelheim W. Germany, Resomer® Resorbable Polyesters.

Low-Molecular-Weight Copolymers Composed of L-Lactic Acid and Various D,L-Hydroxy Acids as Biodegradable Carriers; Fukuzaki, H. et al; Makromol. Chem. 190, 1989, pp. 2571–2577.

Polylactones-18, Polymerization of L,L-Lactide with Sn(II) and Sn(IV) Halogenides; Kricheldorf, H. R.; Eur. Polym. J. vol. 25, No. 6, 1989, pp. 585–591.

The injection molding of resorbable implants; Offergeld, H. et al; Bibliographie ANTEC, 1989, pp. 1282–1286.

Stereo block copolymers of L- and D-lactides; Yui, Nobuhiko et al; Makromol. Chem., 191, 1990, pp. 481–488.

BIODEGRADABLE PACKAGING THERMOPLASTICS FROM LACTIDES

This is a continuation-in-part of copending application Ser. No. 07/387,678 filed on Jul. 31, 1989 now abandoned; which is a continuation-in-part of Ser. No. 07/229,896 filed on Aug. 8, 1988, now abandoned.

FIELD OF THE INVENTION

The present invention relates to plasticized biodegradable polymers of L-lactide, D-lactide, D,L-lactide and mixtures thereof suitable for packaging applications conventionally served by nondegradable plastics (e.g. polyethylene). The invention further relates to a method for producing pliable films and other packaging items from such polymers and to the unique product thereof. The invention has utility in producing a product that has the physical characteristics of the usual film forming plastics, yet is biodegradable.

The present application is related to the application entitled BIODEGRADABLE REPLACEMENT OF CRYSTAL POLYSTYRENE, having Ser. No. 07/579,465, the application entitled BLENDS OF POLYLACTIC ACID, having Ser. No. 07/579,000, and the application entitled DEGRADABLE IMPACT MODIFIED POLYLACTIC ACID, having Ser. No. 07/579,460, all having the same assignee and filing date as the present application, the disclosures of which are incorporated by reference herein.

BACKGROUND OF THE INVENTION

There is a need for an environmentally biodegradable packaging thermoplastic as an answer to the tremendous amounts of discarded plastic packaging materials. U.S. plastic sales in 1987 were 53.7 billion pounds of which 12.7 billion pounds were listed as plastics in packaging. A significant amount of this plastic is discarded and becomes a plastic pollutant that is a blot on the landscape and a threat to marine life. Mortality estimates range as high as 1-2 million seabirds and 100,000 marine mammals per year.

A further problem with the disposal of plastic packaging is the concern for dwindling landfill space. It has been estimated that most major cities will have used up available landfills for solid waste disposal by the early 1990's. Plastics comprise approximately 3 percent by weight and 6 percent of the volume of solid waste.

One other disadvantage of conventional plastics is that they are ultimately derived from petroleum, which leaves plastics dependent on the uncertainties of foreign crude oil imports. A better feedstock would be one that derives from renewable, domestic resources.

However, there are good reasons for the use of packaging plastics. They provide appealing aesthetic qualities in the form of attractive packages which can be quickly fabricated and filled with specified units of products. The packages maintain cleanliness, storage stability, and desirable qualities such as transparency for inspection of contents. These packages are known for their low cost of production and chemical stability. This stability, however leads to very long life of plastic, so that when its one time use is completed, discarded packages remain on, and in, the environment for incalculably long times.

The polymers and copolymers of lactic acid have been known for some time as unique materials since they are biodegradable, biocompatible and thermoplastic. These polymers are well behaved thermoplastics, and are 100 percent biodegradable in an animal body via hydrolysis over a time period of several months to a year. In a wet environment they begin to show degradation after several weeks and disappear in about a year's time when left on or in the soil or seawater. The degradation products are lactic acid, carbon dioxide and water, all of which are harmless.

In practice, lactic acid is converted to its cyclic dimer, lactide, which becomes the monomer for polymerization. Lactic acid is potentially available from inexpensive feedstocks such as cornstarch or corn syrup, by fermentation, or from petrochemical feedstocks such as ethylene. Lactide monomer is conveniently converted to resin by a catalyzed, melt polymerization, a general process well-known to plastics producers. By performing the polymerization from an intermediate monomer, versatility in the resin composition is permitted. Molecular weight can be easily controlled. Compositions can be varied to introduce specific properties.

Homopolymers and copolymers of various cyclic esters such as glycolide, lactide, and the lactones have been disclosed in numerous patents and scientific publications. Early patents disclosed processes for polymerizing lactic acid, lactide, or both, but did not achieve high molecular weight polymers with good physical properties, and the polymer products were frequently tacky, sticky materials. See, for example, U.S. Pat. Nos. 1,995,970; 2,362,511; 2,683,136; and 3,565,869. The Lowe patent, U.S. Pat. No. 2,668,162, teaches the use of pure glycolide and lactide to achieve high molecular weight polymers and copolymers of lactide. Copolymerization of lactide and glycolide imparted toughness and improved thermoplastic processability as compared to the homopolymers. Emphasis was placed on orientable, cold-drawable fibers. Films are described as self-supporting, or stiff, tough, and either clear or opaque. The polymers were high melting and stiff. U.S. Pat. No. 3,565,869 discloses the typical attitude to the presence of monomer in polyglycolide—the removal of the monomer from the product. In U.S. Pat. No. 2,396,994, Filachione et al disclose a process for producing poly(lactic acids) of low molecular weights from lactic acid in the presence of a strong mineral acid catalyst. In U.S. Pat. No. 2,438,208, Filachione et al disclose a continuous process for preparing poly(lactic acid) with an acidic esterification catalyst. In U.S. Pat. No. 4.683,288, Tanaka et al disclose the polymerization or copolymerization of lactic and/or glycolic acid with a catalyst of acid clay or activated clay. The average molecular weight of the polymer is at least 5,000 and preferably 5,000-30,000. In U.S. Pat. No. 4,789,726, Hutchinson discloses a process for production of polylactides or poly (lactide-co-glycolide) of specified low-medium molecular weight, by controlled hydrolysis of a higher molecular weight polyester.

Similar disclosures in the patent and other literature developed the processes of polymerization and copolymerization of lactide to produce very strong, crystalline, orientable, stiff polymers which were fabricated into fibers and prosthetic devices that were biodegradable and biocompatible, sometimes called absorbable. The polymers slowly disappeared by hydrolysis. See, for example, U.S. Pat. Nos. 2,703,316; 2,758,987; 3,297,033; 3,463,158; 3,498,957; 3,531,561; 3,620,218; 3,636,956; 3,736,646; 3,797,499; 3,839,297; 3,982,543; 4,243,775; 4,438,253; 4,496,446; 4,621,638; European Patent Application EP0146398, International Application WO 86/00533, and West German Offenlegungsschrift DE 2118127 (1971). U.S. Pat. Nos. 4,539,981 and 4,550,449 to Tunc teach high molecular weight materials suitable for prosthetic devices, while in EP 321,176 (1989) Tunc discloses a process for orienting resorbable thermoplastic members made from polylactides disclosed in the U.S. patents. U.S. Pat. No. 4.603,695 discloses sheet surgical adhesion preventatives. U.S. Pat. No. 4,534,349 discloses molded medical devices for nerve repair. R. G. Sinclair et al in, Preparation and Evaluation of Glycolic and Lactic Acid-Based for Implant Devices Used in Management of Maxillofacial Trauma, I; AD748410. National Technical Information Service, prepares and evaluates polymers and copolymers of L-lactide and glycolide, the polymers were light brown in the case of the polyglycolide with increasing color in the case of the polymers incorporating more lactide, in a second series of polymers the homopolymer of lactide was a snow white crystalline solid.

Other patents teach the use of these polymers as stiff surgical elements for biomedical fasteners, screws, nails, pins, and bone plates. See, for example, U.S. Pat. Nos. 3,739,773; 4,060,089; and 4,279.249.

Controlled release devices, using mixtures of bioactive substances with the polymers and copolymers of lactide and/or glycolide, have been disclosed. See, for example, U.S. Pat. Nos. 3,773,919; 3,887,699; 4,273,920; 4,419,340; 4,471,077; 4,578,384; in 4,728,721, Yamamoto et al disclose the treatment of biodegradable high molecular weight polymers with water or a mixture of water and water soluble organic solvents so as to remove unreacted monomer or monomers and polymers of low polymerization degree. Poly(lactic acid) and copolymers of lactic and glycolic acid of 2,000 to 50,000 molecular weight are prepared by direct condensation for use as an excipient for microcapsules; R. G. Sinclair, in Environmental Science & Technology, 7 (10), 955 (1973). R. G. Sinclair, Proceedings, 5th International Symposium on Controlled Release of Bioactive Materials, 5.12 and 8.2, University of Akron Press, 1978. These applications of lactide polymers and copolymers required tough, or glassy materials, that were grindable and did not disclose physical properties for obvious use in thermoplastic packaging materials. R. G. Sinclair in, Lactic Acid Polymers—Controlled Release Applications for Biomedical Use and Pesticide Delivery; Proc. of the First Annual Corn Util. Conf., p. 211, Jun. 11–12, 1987, discusses some of the advantages of lactides as homopolymers and as copolymers with glycolide and caprolactones.

Some mention has been disclosed in the prior art for use of lactide copolymers for packaging applications. Thus, in the aforementioned patent to Lowe, clear, self-supporting films are noted of a copolymer of lactide and glycolide. In U.S. Pat. No. 2,703,316 lactide polymers are described as film formers, which are tough and orientable. "Wrapping tissue" was disclosed that was tough, flexible, and strong, or pliable. However, to obtain pliability the polylactide must be wet with volatile solvent, otherwise, stiff and brittle polymers were obtained. This is an example of the prior art which teaches special modifications of lactide polymers to obtain pliability. Thus, in U.S. Pat. No. 3,021,309, lactides are copolymerized with delta valerolactone and caprolactone to modify lactide polymers and obtain tough, white, crystalline solids. Soft, solid copolymer compositions are mentioned only with the copolymer of caprolactone and 2,4-dimethyl-4-methoxymethyl-5-hydroxypentanoic acid lactone, not with lactide compositions. U.S. Pat. No. 3,284,417 relates to the production of polyesters which are useful as plasticizers and intermediates for the preparation of elastomers and foams. This patent excludes lactides and uses compositions based on 7 to 9 membered ring lactones, such as epsilon caprolactone, to obtain the desired intermediates. No tensile strength, modulus, or percent elongation data are given. U.S. Pat. No. 3,297,033 teaches the use of glycolide and glycolide-lactide copolymers to prepare opaque materials, orientable into fibers suitable for sutures. It is stated that "plasticizers interfere with crystallinity, but are useful for sponge and films". Obvious in these disclosures is that the lactide polymers and copolymers are stiff unless plasticized. This is true also of U.S. Pat. No. 3.736,646, where lactide-glycolide copolymers are softened by the use of solvents such as methylene chloride, xylene, or toluene. In U.S. Pat. No. 3,797,499 copolymers of L-lactide and D,L-lactide are cited as possessing greater flexibility in drawn fibers for absorbable sutures. These fibers have strengths greater than 50.000 psi with elongation percentages of approximately 20 percent. Moduli are about one million psi. These are still quite stiff compositions compared to most flexible packaging compositions, reflecting their use for sutures. U.S. Pat. No. 3,844,987 discloses the use of graft and blends of biodegradable polymers with naturally occurring biodegradable products, such as cellulosic materials, soya bean powder, rice hulls, and brewer's yeast, for articles of manufacture such as a container to hold a medium to germinate and grow seeds or seedlings. These articles of manufacture are not suitable for packaging applications.

U.S. Pat. No. 4,620,999 discloses a biodegradable, disposable bag composition comprised of polymers of 3-hydroxybutyrate and 3-hydroxybutyrate/3-hydroxyvalerate copolymer. Lactic acid, by comparison, is 2-hydroxy propionic acid. U.S. Pat. No. 3,982,543 teaches the use of volatile solvents as plasticizers with lactide copolymers to obtain pliability. U.S. Pat. Nos. 4,045,418 and 4,057,537 rely on copolymerization of caprolactone with lactides, either L-lactide, or D,L-lactide, to obtain pliability. U.S. Pat. No. 4,052,988 teaches the use of poly (p-dioxanone) to obtain improved knot tying and knot security for absorbable sutures. U.S. Pat. Nos. 4,387,769 and 4,526,695 disclose the use of lactide and glycolide polymers and copolymers that are deformable, but only at elevated temperatures. European Patent Application 0108933 using a modification of glycolide copolymers with polyethylene glycol to obtain triblock copolymers which are taught as suture materials. As mentioned previously, there is a strong consensus that pliability is obtained in lactide polymers only by plasticizers which are fugitive, volatile solvents, or other comonomer materials.

Copolymers of L-lactide and D,L-lactide are known from the prior art, but citations note that pliability is not an intrinsic physical property. The homopolymers of L-lactide and D,L-lactide, as well as the 75/25, 50/50, and 25/75, weight ratio, of L-/D,L-lactide copolymers are exampled in U.S. Pat. No. 2,951,828. The copolymers have softening points of 110°–135° C. No other physical property data are given relating to stiffness and flexibility. The 95/5, 92.5/7.5, 90/10, and 85/15, weight ratio, of L-lactide/D,L-lactide copolymers are cited in U.S. Pat. Nos. 3,636,956 and 3,797,499. They are evaluated as filaments from drawn fibers and have tensile strengths in excess of 50,000 psi, moduli of about one million psi, and percent elongations of approximately 20 percent. Plasticizers, the same as in U.S. Pat. No. 3,636,956, above, were used to impart pliability. A snow-white, obviously crystalline polymer, is cited in Offenlegungsschrift 2118127 for a 90/10, L-lactide/D,L-lactide copolymer. No physical properties were given for this copolymer. The patent teaches the use of surgical elements.

Canadian Patent 808,731 cites the copolymers of L- and D,L-lactide where a divalent metal of Group II is part of the structure. The 90/10, L-/D,L-lactide copolymer (Example 2) and the L-lactide homopolymer were described as "suitable for films and fibers". The 90/10 copolymer is described as a snow-white copolymer and the homopolymer of L-lactide can be molded to transparent films. (The more crystalline polymer should be the opaque, or snow-white material, which is the homopolymer.) The patent discloses "the fact that the novel polylactides of the present invention contain the metallic component of the catalyst in the form of a lactate is believed to be of significance". Furthermore, "the polylactides find utility in the manufacture of films and fibers which are prepared by conventional thermoplastic resin manufacturing methods". No physical property data are given on the strength and flexibility of the films.

Canadian Patent 863,673 discloses compositions of L-lactide and D,L-lactide copolymers in the ratios of 97/3, 95/5, 92.5/7.5, 90/10, and 85/15 ratios of L-/D,L-lactide, respectively. These were all characterized as drawn filaments for surgical applications. Tensile strength, approximately 100,000 psi, was high, elongation was approximately 20 percent and plasticizers were mentioned to achieve pliability. D,L-lactide compositions of less than 15 weight percent are claimed.

Canadian Patent 923,245 discloses the copolymers of L- and D,L-lactide (Example 15). The 90/10 copolymer is described as a snow white polylactide. The polylactides prepared by the methods of the patent are stated to have utility in the manufacture of films or fibers prepared by conventional thermoplastic resin fabricating methods.

U.S. Pat. No. 4,719,246 teaches the use of simple blending of poly L-and poly (D-lactide), referred to as poly (S-lactide) and poly (R-lactide). The examples are all physical mixtures. The special properties of the "interlocking" stem from racemic compound formation (cf. "Stereochemistry of Carbon Compounds", E. L. Eliel, McGraw-Hill, 1962, p. 45). Racemic compounds consist of interlocked enantiomers, that is, the D and L forms (or R and S) are bonded to each other by polar forces. This can cause a lowering, or raising, of the crystalline melting points, depending on whether the D to D (or L to L) forces are less, or greater, than the D to L forces. Required of polymer racemic compounds to enhance the effect (and stated in U.S. Pat. No. 4,719,246, Column 4, line 48) are homopolymers, or long chain lengths, of both D and L. The great symmetry or regularity of these structures permit them to fit together, or interlock, by very regular polar forces, either because they are the same, or mirror images. This leads to considerable crystallinity. The art of racemic compounds has a long history that goes back to classical chemistry.

Additional related art includes: Low molecular weight poly D,L-lactide has been recently added to high molecular weight D,L-lactide along with a drug such as caffeine, salicylic acid, or quinidine, see R. Bodmeier et al, International J. of Pharm. 51, pp. 1-8, (1989). Chabot et al in polymerizing L-lactide and racemic D,L-lactide for medical applications removed residual monomer and lower oligomers, see Polymer, Vol. 24, pp. 53-59, (1983). A. S. Chawla and Chang produced four different molecular weight D,L-lactide polymers but removed monomer for in vivo degradation studies, see Biomat., Med. Dev. Art. Org., 13(3&4), pp. 153-162, (1985-86). Kleine and Kleine produce several low residual monomer, poly(lactic acids) from D,L-lactide while determining lactide levels during the polymerization, see Macromolekulare Chemie, Vol. 30, pp. 23-38, (1959); Kohn et al also makes a low residual monomer product while monitoring the monomer content over time, see Journ. Appl. Polymer Science, Vol. 29, pp. 4265-4277, (1984). M. Vert et al teaches high molecular weight polylactides with elimination of residual monomer, see Makromol. Chem., Suppl. 5, pp. 30-41, (1981). M. Vert, in Macromol. Chem., Macromol. Symp. 6, pp.109-122, (1986), discloses similar poly(L-/D,L-lactide) polylactides, see Table 6, p. 118. In EP 311,065 (1989) poly D,L-lactide is prepared as an implant material for drug delivery as the material degrades, the material contains drugs, low molecular weight polylactide, and other additives; EP 314,245 (1989) teaches a polylactide having a low amount of residual monomer, the polymer is prepared by polymerization of meso D,L-lactide or other monomers; West German Offenlegungsschrift DE 3,820,299 (1988) teaches the polymerization of meso D,L-lactide with lactides, however, the advantages of the present invention are not obtained.

Nowhere in the prior art is it disclosed that lactic acid or lactide polymers, can be the source of pliable, highly-extensible compositions by the use of lactide monomers, or lactic acid, or oligomers of lactic acid, or derivatives of oligomers of lactic acid, or oligomers of lactide as the plasticizer. None of the prior compositions are suitable for well-defined packaging needs.

BRIEF DESCRIPTION OF THE INVENTION

The general teaching of the invention is that poly(lactic acids) derived from lactic acid (homopolymers or copolymers of L-lactic acid or D-lactic acid) or lactides (homopolymers or copolymers of L-lactide, D-lactide, meso D,L-lactide, and racemic D,L-lactide) that have been intimately plasticized with a plasticizer such as lactic acid, lactide, oligomers of lactic acid, oligomers of lactide, derivatives of oligomeric lactic acid (as used herein this term includes derivatives of oligomeric lactide), and various mixtures thereof, have utility as well behaved thermoplastics which can mimic properties of the usual environmentally very slowly degradable plastics, (e.g., the properties of polyethylene and the like). The term, intimately dispersed, as used herein means the material is homogeneously and intimately mixed with the polymer. Since both lactic acid and lactide can achieve the same repeating unit, the general term poly(lactic acid) as used herein refers to polymers having the repeating unit of formula I without any limitation as to how the polymer was made (e.g. from lactides, lactic acid, or oligomers), and without reference to the degree of polymerization or level of plasticization.

In general, a first embodiment of the invention provides for an environmentally biodegradable composition useful as a replacement for thermoplastic polymer compositions comprising a poly(lactic acid), and a plasticizer selected from the groups below, wherein the plasticizer is intimately dispersed within the polymer. The poly(lactic acid) polymer has the repeating units of the formula,

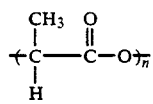

wherein n is the number of repeating units and n is an integer equal to at least about 150. Preferably the unoriented composition has the physical properties of: $150 \leq n \leq 20,000$, a tensile strength of about 300 to about 20,000 psi, an elongation to failure of about 50 to about 1,000 percent, and a tangent modulus of about 20,000 to about 250,000 psi. The intimate dispersion of the plasticizer can yield a substantially transparent composition, although, transparency may not be obtained with certain processes as when the composition is foamed.

In a further embodiment the composition can be a replacement for polyethylene when the unoriented composition has a tensile strength of about 1,200 to about 4,000 psi, an elongation to failure of about 100 to about 800 percent, and a tangent modulus of about 20,000 to about 75,000 psi. The composition can be a replacement for polypropylene when the unoriented composition has a tensile strength of about 4,500 to about 10,000 psi, an elongation to failure of about 100 to about 600 percent, a tangent modulus of about 165,000 to about 225,000 psi, and a melting point of about 150° C. to about 190° F.

A further embodiment of the invention provides a process for producing an environmentally biodegradable composition useful as a replacement for thermoplastic polymer compositions having the steps (a) polymerizing a lactide monomer selected from the group consisting of D-lactide, L-lactide, meso D,L-lactide, racemic D,L-lactide, and mixtures thereof, in the presence of a suitable catalyst; (b) controlling the polymerization to allow the reaction to be stopped prior to complete polymerization; (c) monitoring the level of remaining monomer; (d) stopping the polymerization prior to complete reaction so that unreacted monomer in a predetermined amount is trapped in association with the polymer; and (e) treating the polymer and unreacted monomer to obtain an intimately plasticized composition. The polymerization reaction is preferably stopped at a monomer level up to about 40 weight percent. If desired, additional plasticizer may be incorporated into the composition prior to, during, or after the treating step, wherein the plasticizer is selected from the group of plasticizers discussed below. The sum of remaining monomer and additional plasticizer is preferably below about 40 weight percent, and is most preferably between about 10 and about 40 weight percent for a pliable composition.

A yet further embodiment includes a process for producing a plasticized polymer of poly(lactic acid) that comprises mixing, heating, and melting one or more lactide monomers and a catalyst; polymerizing the monomers of the solution to form a polymer without stopping the reaction; and incorporating plasticizer as described below into the formed polymer.

A yet further embodiment includes a process for providing a poly(lactic acid) to which the described plasticizers may be added to obtain the desired properties.

A yet further embodiment includes a process for the preparation of a biodegradable blown film through the inclusion of the below listed plasticizers in poly(lactic acid) to achieve desired properties followed by extrusion of the plasticized poly(lactic acid) as a blown film.

Plasticizers useful with the invention include lactic acid, lactide, oligomers of lactic acid, oligomers of lactide, and mixtures thereof. The preferred oligomers of lactic acid, and oligomers of lactide are defined by the formula:

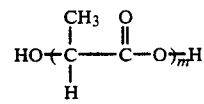

where m is an integer: $2 \leq m \leq 75$. Preferably m is an integer: $2 \leq m \leq 10$.

Further plasticizers useful in the invention include oligomeric derivatives of lactic acid, selected from the group defined by the formula:

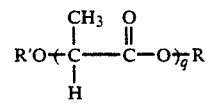

where R = H, alkyl, aryl, alkylaryl or acetyl, and R is saturated, where R' = H, alkyl, aryl, alkylaryl or acetyl, and R' is saturated, where R and R' cannot both be H, where q is an integer: $2 \leq q \leq 75$; and mixtures thereof. Preferably q is an integer: $2 \leq q \leq 10$.

For pliability, lactic acid or lactide monomer plasticizer is present in an amount of from about 10 to about 40 weight percent of the polymer, while plasticizers such as oligomers of lactide, or oligomers of lactic acid, and derivatives of oligomers of lactic acid may be present in an amount from about 10 to about 60 weight percent. This composition allows many of the desirable characteristics of nondegradable polymers, e.g. polyethylene, such as pliability, transparency, and toughness. In addition, the presence of plasticizer facilitates melt processing, prevents discoloration, and enhances the degradation rate of the compositions in contact with the environment.

The intimately plasticized composition should be processed into a final product in a manner adapted to retain the plasticizer as an intimate dispersion in the polymer. The treatments to obtain an intimate dispersion include: (1) quenching the composition at a rate adapted to retain the plasticizer as an intimate dispersion; (2) melt processing and quenching the composition at a rate adapted to retain the plasticizer as an intimate dispersion; and (3) processing the composition into a final product in a manner adapted to maintain the plasticizer as an intimate dispersion.

The composition may comprise from about 2 to about 60 weight percent plasticizer. When a lactide is selected, the composition preferably comprises from about 10 to about 40 weight percent lactide plasticizer selected from the group consisting of lactic acid, D-lactide, L-lactide, meso D,L-lactide, racemic D,L-lactide, and mixtures thereof.

If desired, the plasticizer can be selected from the group of lactides consisting of D-lactide, L-lactide, meso D,L-lactide, racemic D,L-lactide and mixtures thereof so that at least part of the lactide plasticizer is stereochemically different from the monomer used to prepare the polymer. Similarly the plasticizer may comprise oligomers of lactide, or oligomers of lactic acid, or mixtures thereof, having the formula II, that are not produced during the production of the polymer.

Particularly advantageous is the sequential incorporation of plasticizer into poly(lactic acid) to obtain a blended composition by melt blending with the poly(lactic acid), a first plasticizer selected from the group consisting of oligomers of lactic acid, oligomers of lactide, and mixtures thereof; and melt blending with the blend a second plasticizer selected from the group consisting of lactic acid, L-lactide, D-lactide, meso D,L-lactide, racemic D,L-lactide, and mixtures thereof. If desired, a first plasticizer defined by the formula III may be used alone or in admixture with an oligomer of formula II. This procedure allows the blending of the first plasticizer at a first temperature and the blending of the second plasticizer at a second temperature lower than the first temperature.

DETAILED DESCRIPTION OF THE INVENTION AND PREFERRED EMBODIMENTS

Figure 1:
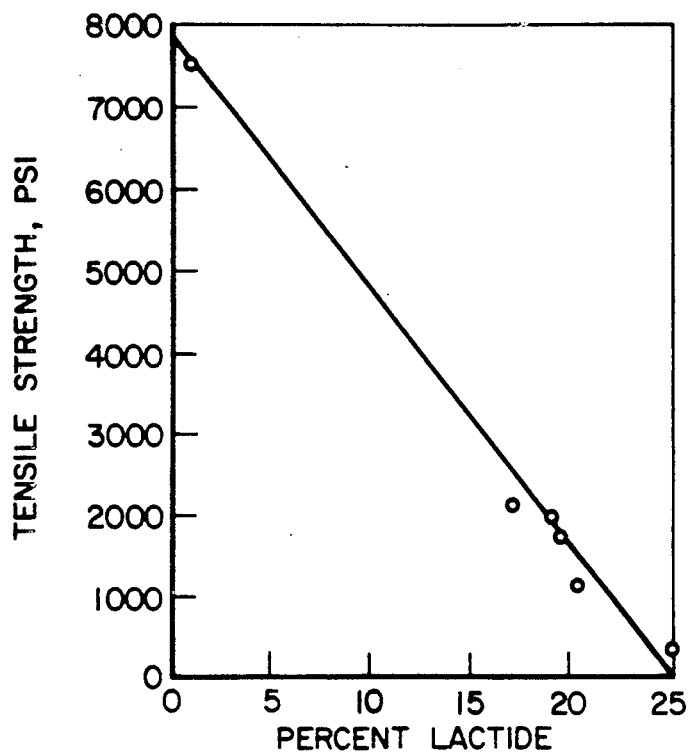
FIG. 1 is a graph showing the relationship between percent lactide in the composition as plasticizer and tensile strength.

The environmentally biodegradable compositions disclosed herein are completely degradable to environmentally acceptable and compatible materials. The intermediate products of the degradation, lactic acid, and short chain oligomers of lactide or lactic acid are widely distributed naturally occurring substances that are easily metabolized by a wide variety of organisms. Their natural end degradation products are carbon dioxide and water. Contemplated equivalents of these compositions such as those that contain minor amounts of other materials, fillers, or extenders can also be completely environmentally degradable by proper choice of materials. The compositions herein provide environmentally acceptable materials because their physical deterioration and degradation is much more rapid and complete than the conventional nondegradable plastics that they replace. Further, since all or a major portion of the composition will be poly(lactic acid), and/or a lactic acid derived lactide or oligomer, no residue or only a small portion of more slowly degrading residue will remain. This residue will have a higher surface area than the bulk product and an expected faster degradation rate.

The general application of the invention results in the first and general embodiment of the invention. The homopolymers of D-lactide, L-lactide, D,L-lactide as well as copolymers of D-lactide, L-lactide; D-lactide, D,L-lactide; L-lactide, D,L-lactide; and D-lactide, L-lactide, and D,L-lactide all produce materials useful in the invention when plasticized by lactide monomers, lactic acid, oligomers of lactide, oligomers of lactic acid, derivatives of oligomeric lactic acid and mixtures thereof that are intimately dispersed in the polymer. A plasticizer may be produced by stopping the reaction before polymerization is completed. Optionally additional plasticizer consisting of lactide monomers (D-lactide, L-lactide, D,L-lactide, or mixtures thereof), lactic acid, oligomers lactide or oligomers of lactic acid or its derivatives including all L-, D-, and DL- configurations and mixtures thereof can be added to the formed polymer. While aspects of the invention can be applied to various polylactides in general, one preferred polymer is defined by the formula:

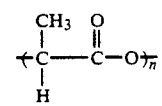

where n is the degree of polymerization (number of repeating units), plasticized with a plasticizer derived from incomplete polymerization of the monomers used to produce the polymer. The more intimately the plasticizer is integrated within the polymer the better are its characteristics. In fact very intimate integration is needed to obtain the advantages of the invention further discussed below. If desired, additional monomer or oligomer plasticizer can be added to any residual monomer or oligomer remaining in the composition after polymerization. The preferred oligomers of lactic acid, and oligomers of lactide including all L-, D-, DL- configurations and mixtures thereof, both random and block configurations, useful for a plasticizer are defined by the formula:

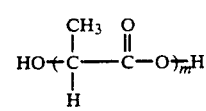

where m is an integer: $2 \leq m \leq 75$. Preferably m is an integer: $2 \leq m \leq 10$. The oligomers of lactic acid and its derivatives including all L-, D-, DL- configurations and mixtures thereof, both random and block configurations, useful for a plasticizer are defined by the formula III:

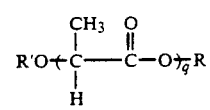

where R=H, alkyl, aryl, alkylaryl or acetyl, and R is saturated, and where R'=H, alkyl, aryl, alkylaryl or acetyl, and R' is saturated, where R and R' cannot both be H, where q is an integer: $2 \leq q \leq 75$; and mixtures thereof. Preferably q is an integer: $2 \leq q \leq 10$.

The plasticizers added to the polymer compositions have the following functions:
(a) They act as plasticizers introducing pliability and flexibility into the polymer compositions not found in polymer-only composition.
(b) Addition of these plasticizers to the poly(lactic acid) reduces the melt viscosity of the polymers and lowers the temperature, pressure, and shear rate required to melt form the compositions.
(c) The plasticizers prevent heat build up and consequent discoloration and molecular weight decrease during extrusion forming of poly(lactic acid).
(d) The plasticizers add impact resistance to the compositions not found in the polymer alone.

In addition, the plasticizers may act as compatibilizers for melt-blends of polylactides and other degradable and nondegradable polymers. That is, molten mixtures of two different polymers can more intimately associate and mix into well dispersed blends in the presence of the plasticizers. The plasticizers may also improve performance in solution blending.

The subscripts n, m, and q above refer to the average number of mers (the repeating unit) of the polymer or oligomer. Number average molecular weight $M_n$ as used herein is related to the mers by multiplying n, m, or q by the molecular weight of the individual mer, for poly(lactic acid) this number is 72. The number of mers present in a polymer is also called the degree of polymerization. The reader is referred to the following texts where this subject is discussed further *Polymer Chemistry an Introduction*, 2nd Edition, R. Seymour et al, Marcel Dekker, Inc., 1988 and *Introduction to Polymer Chemistry*, R. Seymour, McGraw-Hill, New York, 1971.

The proportions of L-lactide, D-lactide, and D,L-lactide in the polymer are not critical to obtaining flexible thermoplastics; however, the proportions of D,L-lactide may vary certain properties as further discussed below. The parts of L-lactide, D-lactide, and D,L-lactide can vary over a wide, weight-ratio to form a homopolymer or copolymer. The lactide monomers employed in accordance with the invention are available commercially so that neither the monomeric reactant per se nor the method by which it is prepared constitute any portion of the invention.

D-lactide is a dilactone, or cyclic dimer, of D-lactic acid. Similarly, L-lactide is a cyclic dimer of L-lactic acid. Meso D,L-lactide is a cyclic dimer of D- and L-lactic acid. Racemic D,L-lactide comprises a mixture of D-lactide and L-lactide. When used alone herein, the term "D,L-lactide" is intended to include meso D,L-lactide or racemic D,L-lactide.

One of the methods reported in the literature for preparing a lactide is to dehydrate lactic acid under high vacuum. The product is distilled at a high temperature and low pressure. Lactides and their preparation are discussed by W. H. Carothers, G. L. Dorough and M. J. Johnson (J. Am. Chem. Soc. 54, 761–762 [1932]); J. Gay-Lussac and J. Pelouse (Ann. 7, 43 [1833]); C. A. Bischoff and P. Walden (Chem. Ber. 26, 263 [1903]; Ann. 279, 171 [1984]); and Heinrich Byk (Ger. Pat. 267,826 [1912]); through Chem. Abstr. 8, 554, 2034 [1914]).

The optically active acids can be prepared by direct fermentation of almost any nontoxic carbohydrate product, by-product or waste, utilizing numerous strains of the bacterial genus Lactobacillus. e.g. *Lactobacillus delbrueckii, L. salivarius. L. casei*, etc. The optically active acids can also be obtained by the resolution of the racemic mixture through the zinc ammonium salt, or the salt with alkaloids, such as morphine. L-lactide is a white powder having a molecular weight of 144. If an impure, commercially-available product is employed in accordance with the present invention, it is preferable to purify it by recrystallization from anhydrous methyl isobutyl ketone. The snow-white crystals of L-lactide melt at 96°–98° C. As used herein the symbol C denotes degrees Centigrade and replaces the symbol °C., similarly the symbol F denotes degrees Fahrenheit and replaces the symbol °F.

D,L-lactic acid which is used in the preparation of D,L-lactide is available commercially. The D,L-lactic acid can be prepared synthetically by the hydrolysis of lactonitrile (acetaldehyde cyanohydrin) or by direct fermentation of almost any nontoxic carbohydrate product, by-product or waste, utilizing numerous strains of the bacterial genus Lactobacillus. D,L-lactide is a white powder having a molecular weight of 144. If an impure, commercially-available product is employed in accordance with the present invention, it is preferable to purify it by recrystallization from anhydrous methyl isobutyl ketone. One such commercially available product comprising a mushy semisolid melting at 90°–130° C. was recrystallized from methyl isobutyl ketone and decolorized using charcoal. After three such recrystallizations, the product was tumble-dried in vacuo under a nitrogen bleed for 8 to 24 hours at room temperature. The snow white crystals thus obtained comprise a D,L-lactide mixture melting from 115°–128° C.

In preparing the compositions in accordance with the invention, it is preferred to carry out the reaction in the liquid phase in a closed, evacuated vessel in the presence of a tin ester of a carboxylic acid containing up to 18 carbon atoms. The compositions however, can also be prepared at atmospheric pressure with the polymerization system blanketed by an inert gas such as, for example, nitrogen. If polymerization is conducted in the presence of oxygen or air, some discoloration occurs with a resulting decrease in molecular weight and tensile strength. The process can be carried out at temperatures where the polymerization is sluggish in its later stages so as to trap residual monomer in the viscous polymer melt. Preferred temperatures for this purpose are generally between the melting points of pure L-lactide and pure D,L-lactide, or between 95° to 127° C. While in no way wishing to limit the scope of the invention it is presently believed that below about 129° C., the following occurs:

1. The reactant lactide monomer mixture of L- and D,L-lactide monomers melt to form a eutectic mixture, which melts to a mobile fluid that is an intimate solution of one, two, or three monomers.
2. The fluid melt is polymerized by catalyst to form an increasingly viscous solution and eventually unreacted monomer is trapped in association with the polymer as a solution, rather than as a distinct heterogeneous phase. The monomer no longer can react since the reaction is extremely diffusion controlled and cannot efficiently contact the low concentration of active end-groups of the polymer.

3. The polymerization ceases or slows considerably so that at room temperature the blend of monomer and polymer are a solid solution that imparts plasticization, clarity, and flexibility to the composition.
4. The catalyst deactivates so that subsequent melt-fabrication does not reinitiate the polymerization.
5. The plasticized composition is quite stable since the residual monomer is very high boiling, e.g., lactide has a boiling point of 142° C. at 8 torr, and is tightly associated with its open-chain tautomer, polylactide.

Alternatively, the process can be carried out at any temperature between the melting point of the L-lactide and 200° C. and lactic acid or lactide is subsequently melt or solvent-blended into the polymer as a further processing step. Temperatures above 200° C. are undesirable because of the tendency of the copolymer to be degraded. Increasing the temperature within the range of 95° to 200° C. generally increases the speed of the polymerization. Good results are obtained by heating a mixture of L-lactide and D,L-lactide at a temperature between about 110° C. and 160° C.

The catalysts employed in accordance with the invention are tin salts and esters of carboxylic acids containing up to 18 carbon atoms. Examples of such acids are formic, acetic, propionic, butyric, valeric, caproic, caprylic, pelargonic, capric, lauric, myristic, palmitic, stearic and benzoic acids. Good results have been obtained with stannous acetate and stannous caprylate.

The catalyst is used in normal catalytic amounts. In general, a catalyst concentration in the range of about 0.001 to about 2 percent by weight, based on the total weight of the L-lactide and D,L-lactide is suitable. A catalyst concentration in the range of about 0.01 to about 1.0 percent by weight is preferred. Good results were obtained when the catalyst concentration is in the range of about 0.02 to about 0.5 percent by weight. The exact amount of catalyst in any particular case depends to a large extent upon the catalyst employed and the operating variables including time and temperature. The exact conditions can be easily determined by those skilled in the art.

The reaction time of the polymerization step, per se, is governed by the other reaction variables including the reaction temperature, the particular catalyst, the amount of catalyst and whether a liquid vehicle is employed. The reaction time can vary from a matter of minutes to a period of hours, or days, depending upon the particular set of conditions which are employed. Heating of the mixture of monomers is continued until the desired level of polymerization is detected. The level of polymerization can be determined by analysis for residual monomers. As discussed previously, the reaction temperature can be chosen to enhance the incorporation of monomer and provide plasticized compositions coming directly out of the polymerization reactor. The reaction can be halted at such time that the composition has attained the conversion of monomer to polymer that is desired to achieve the desired plasticization. In the preferred embodiment of the invention, approximately 2 to 30 percent lactide is left unreacted, depending on the degree of plasticization to be achieved.

In general it is preferred to conduct the polymerization in the absence of impurities which contain active hydrogen since the presence of such impurities tends to deactivate the catalyst and/or increase the reaction time. It is also preferred to conduct the polymerization under substantially anhydrous conditions.

The copolymers of the invention can be prepared by bulk polymerization, suspension polymerization or solution polymerization. The polymerization can be carried out in the presence of an inert normally-liquid organic vehicle such as, for example, aromatic hydrocarbons, e.g.. benzene, toluene, xylene. ethylbenzene and the like; oxygenated organic compounds such as anisole, the dimethyl and diethyl esters of ethylene glycol; normally-liquid saturated hydrocarbons including open chain, cyclic and alkyl-substituted cyclic saturated hydrocarbons such as hexane, heptane, cyclohexane, alkylcyclohexanes, decahydronaphthalene and the like.

The polymerization process can be conducted in a batch, semi-continuous, or continuous manner. In preparing the lactide monomeric reactants and catalyst for subsequent polymerization, they can be admixed in any order according to known polymerization techniques. Thus, the catalyst can be added to either of the monomeric reactants. Thereafter, the catalyst-containing monomer can be admixed with the other monomer. In the alternative, the monomeric reactants can be admixed with each other. The catalyst can then be added to the reactant mixture. If desired, the catalyst can be dissolved or suspended in an inert normally-liquid organic vehicle. If desired, the monomeric reactants either as a solution or a suspension in an inert organic vehicle can be added to the catalyst, catalyst solution or catalyst suspension. Still further, the catalyst and the monomeric reactants can be added to a reaction vessel simultaneously. The reaction vessel can be equipped with a conventional heat exchanger and/or a mixing device. The reaction vessel can be any equipment normally employed in the art of making polymers. One suitable vessel, for example, is a stainless steel vessel.

The environmentally biodegradable compositions produced in accordance with the present invention depending upon the L-lactide, D-lactide, meso D,L-lactide ratios, find utility in articles of manufacture, such as films, fibers, moldings and laminates, which are prepared by conventional fabricating methods. These articles of manufacture are contemplated for nonmedical uses i.e. outside the body where they can substitute for the common environmentally nondegradable plastics.

Filaments, for example, are formed by melt-extruding the copolymer through a spinneret. Films are formed by casting solutions of the biodegradable compositions and then removing the solvent, by pressing solid biodegradable compositions in a hydraulic press having heated platens, or by extrusion through a die, including Blown Film techniques.

Various techniques including melt blending, slow cooling, and rapid cooling (quenching) can be employed in preparing products e.g. moldings from the polymers and copolymers of the invention.

Quenching as used herein indicates that the temperature is dropped rapidly to prevent extensive crystallization of the polymer. Crystallization of polymers is a slow process, requiring minutes to hours to fully accomplish. When this is desired, the temperature is held above the glass-transition temperature, $T_g$, for some time to allow the molecules to order themselves into extensive crystalline lattices. This is called annealing. When cooled rapidly from an amorphous melt, the polymer does not have the time required and remains largely amorphous. The time required to quench depends on the thickness of the sample, its molecular weight, melt viscosity, composition, and its Tg, where it is frozen-in as a glassy state. Note that melt viscosity and Tg are lowered by plasticization and favor quenching. Thin films obviously cool very quickly because of their high surface-to-volume ratio while molded items cool more slowly with their greater thicknesses and time spent in a warm mold before removal. Regular structures such as poly (L-lactide) order more easily and crystallize more quickly than more random structures such as a copolymer.

With the polylactides the melting points are approximately 150°-190° C. depending on the L-lactide content and, therefore, the regularity of structure. The Tg of all the polylactides, including various L and D,L homopolymers and copolymers is 60° C. The Tg decreases when residual lactide is intimately dispersed with the polymer. Quenching to an amorphous state requires that the polymer or copolymer in an amorphous melt is rapidly cooled from its molten state to a temperature below its Tg. Failure to do so allows spherulitic crystallinity to develop, that is, crystalline domains of submicron to micron size. The latter scatters light and the polymer specimens become opaque. These crystalline forms have improved stability to heat distortion. This spherulitic crystallinity is often called short range order-long range disorder since the crystallites are separated by amorphous regions. However, the crystallites act as pseudo crosslinks to maintain dimensional stability above the Tg but below their melting points. Alternatively stability to heat distortion can be obtained by orienting an amorphous polymer above its Tg but below its melting point. Here, the polymer molecules are stretched to allow some long range ordering, then "heat set" to permit the ordering to complete, that is, given some time to anneal. The amorphous polymer is thereby crystallized into a different order, called long-range order, short range disorder. Transparency and resistance to heat distortion are favored.

A detailed discussion can be found in textbooks, for example, "Structural Polymer Properties", by Robert J. Samuels, Wiley Publications, New York, N.Y. 1974.

Contemplated equivalents of the compositions of the invention are those that contain minor amounts of other materials. The copolymers produced in accordance with the present invention can be modified, if desired, by the addition of a cross-linking agent, other plasticizers, a coloring agent, a filler and the like, or minor amounts of other lactone monomers such as glycolide or caprolactone.

Cross-linking can be effected by compounding the compositions with free-radical initiators such as cumene hydroperoxide and then molding at elevated temperatures. This can improve heat-and solvent-resistance. Curing can also be effected by compounding the copolymers with multifunctional compounds such as polyhydric alcohols and molding, or thermoforming under heat and vacuum. Graft-extruder reactions to effect curing of the polyesters is an obvious method of cross-linking and chain-extending the copolymers.

In preparing moldings, a filler can be incorporated in the compositions prior to curing. A filler has the function of modifying the properties of a molding, including hardness, strength, temperature resistance, etc. Known filler materials include aluminum powder, powdered calcium carbonate, silica, kaolinite (clay), magnesium silicate and the like. Of particular advantage is starch, which blends well with the compositions to obtain a blend which is totally environmentally biodegradable.

Other property modifications can be effected by melt blending the compositions with other polymers and copolymers of the lactides, glycolides, and caprolactones.

The compositions prepared according to the present invention can be used in producing reinforced laminates according to known procedures. In general, laminates are made from a fibrous mat or by assembling a multiplicity of sheets of material to form a matrix which is consolidated into a unitary structure by flowing molten precursor or composition through the fibrous material and curing it while in a mold or hydraulic press to form the polymer. Fibers which are used in forming the matrix include natural and synthetic fibers such as cellulose derived from wood, cotton, linen, hemp, and the like, glass, nylon, cellulose acetate and the like.

The compositions of the invention and their preparation are further illustrated by the following specific examples.

EXAMPLE 1

80/20, L-lactide/racemic D,L-lactide 160 grams of L-lactide and 40 grams of racemic D,L-lactide, both of high purity (Purac, Inc., triply recrystallized), were charged into a 500 ml, round-bottom flask and purged with dry nitrogen overnight. 10 ml of stannous octoate is dissolved in 60 ml of anhydrous toluene, and 10 ml of the solvent is distilled to a Dean-Stark trap to effect dryness of this catalyst solution by azeotropic distillation. From the 10 ml of stannous octoate in 50 ml of dry toluene a 0.20 ml portion is removed with a syringe and injected into the lactides in the reaction flask. The nitrogen purge is continuous via a syringe needle connection that enters the reaction flask through a rubber septum and vents via a piece of tubing that connects to a bubbler. The nitrogen flow is maintained at 1-3 bubbles per second. The flask was heated in an oil bath maintained at 123°-127° C. During the first part of the heating the lactides melt and are mixed thoroughly by swirling. Thereafter, the products become quite viscous. After 20 hours of heating, the flask and the colorless, transparent products are removed from the heating bath, cooled, the flask broken, and shocked with liquid nitrogen to remove glass from the product. The copolymer was molded in a heated hydraulic press. Compression molding to 5 to 10 mil thick films was possible at 20,000 lb pressure, at 170° C., in a time period of 2 minutes. The films were evaluated for their tensile properties on a Instron tester, and the results are listed in Table 1. Samples ⅛ inch thick were also molded for impact strength testing. A thermogravimetric analysis of the product was performed, noting the weight loss upon heating the sample to 150° C. in 4 minutes and holding the temperature at 150° C. for 60 minutes. The weight loss of the sample was 19.5 percent and nearly complete in 60 minutes. The weight loss is attributed to loss of lactide monomer. Results of differential scanning calorimetry reveal that the composition has an endotherm beginning about 110° C., becoming more pronounced as the temperature increases to 200° C. No melting point was observed. Specimens were annealed at 185° F. overnight and reexamined. They remained transparent, colorless and pliable. Samples of the copolymer could not be remolded 6 times without any discoloration or obvious loss of strength. Thin films were clear, transparent, colorless, and quite flexible, despite the repeated molding.

TABLE 1

PROPERTIES OF COPOLYMERS[a] OF L-LACTIDE AND D,L-LAcTIDE WHEN PLASTICIZED BY LACTIDE

| Example No. | 1 | 2 | 3 |
|---|---|---|---|
| Film thickness, mil | 8 | 8 | 10 |
| Tensile strength, 1000 psi, ASTM D638 | 3.9 | 1.7 | 7.9 |
| Elongation, percent | 280 | 806 | 3.5 |
| 100 percent modulus, 1000 psi | 0.74 | — | — |
| 200 percent modulus, 1000 psi | 1.20 | — | — |
| Tangent modulus, 1000 psi | 36.6 | — | 289 |
| Izod impact strength, ft-lb./in.[b] | 0.63 | — | 0.4 |
| $M_w$, 1000's | 540 | 281 | 341 |
| $M_n$, 1000's | 270 | 118 | 97.5 |
| Residual lactide,[c] percent | 19.5 | 27.8 | 2.7 |

[a]80/20, weight ratio, of L-/racemic D,L-lactide.
[b]⅛ inch, notched samples.
[c]By isothermal thermogravimetric analysis weight loss at 150 C.

EXAMPLE 2

In a 3-liter, round-bottom flask was charged 1.84 Kg of L-lactide, 0.46 Kg of racemic D,L-lactide and 2.3 ml of the stannous octoate solution, similar to Example 1. The mixture was purged with argon for 3 hours, then heated isothermally in a 125° C. oil bath. The mixture melts, was mixed thoroughly by swirling, and forms a homogeneous, transparent, colorless fluid whose viscosity increases substantially after several hours. After 64 hours the flask was removed from the heating bath, cooled, and the glass removed from the clear, transparent, solid product. The rubbery composition was guillotined into slices and ground to ⅛ inch, or smaller, size in a grinder with dry ice. The grind was dried in an air circulating oven at 100° F. for several hours, then vacuum dried overnight at ambient temperature. Compression-molded films were prepared as described in Example 1 and the films were examined for their tensile properties and weight loss by thermogravimetric analysis as shown in Table 1.

EXAMPLE 3

In a 250-ml, round bottom flask was placed 79.98 g of L-lactide, 20.04 g of racemic D,L-lactide, and 0.20 ml of stannous octoate solution, similar to Example 1. The flask was swept by nitrogen through inlets and outlets and heated in a 125° C. oil bath. The mixture melted to a colorless and fluid liquid that was thoroughly mixed by swirling the flask. After 2 hours, the oil bath temperature was increased to 147° C., and after 14 hours total heating time, the temperature was decreased to 131° C. Total heating time was 18 hours. The product is transparent, colorless, and glassy. It was evaluated, similar to the preceding examples and the results are recorded in Table 1.

Examples 1 to 3 reveal the effect of reaction temperature on the properties of the copolymers as occasioned by the resulting composition.

EXAMPLE 4

Films of the copolymers of Examples 1 and 3 were immersed in water for several months. After 3 weeks, the copolymer of Example 1 became hazy while that of Example 3 remained clear for approximately 2 months; after 3 months the film of Example 3 became noticeably hazy and the film of Example 1 is white and opaque. The water that had been in contact with the film of Example 1 tastes acidic while that of Example 3 is tasteless.

Inspection of the data of Table 1 reveals that the copolymer of Example 1 is an environmentally biodegradable replacement for polyethylene. Those skilled in the art will recognize that the physical properties of the copolymer are an excellent combination useful for many packaging applications. Its tensile strength and initial tangent modulus compare favorably with polyethylene compositions used, for example, in plastic trash bags, general film wrap, plastic shopping bags, sandwich wrap, six pack yokes and the like. The shape of the stress-strain curves are approximately the same for both the copolymer and that for a linear low density polyethylene composition commonly used in trash bag compositions. A comparison of properties are shown in Table 2.

TABLE 2

COMPARISON OF POLYETHYLENE TO POLYLACTIC ACID

| Property | LDPE-[a] NA 272 | LLDPE[b] | Lactide Copolymer[c] |
|---|---|---|---|
| Tensile strength, 1000 psi, ASTM Standard C | 2.18 | 2.9 | 3.90 |
| Elongation, % | 261 | 500 | 280 |
| Tangent modulus, 1000 psi | 54.9 | 51.0 | 36.6 |
| 100% modulus, 1000 psi | 1.77 | — | 0.74 |
| 200% modulus | 1.82 | — | 1.20 |
| HDT,[d] 264 psi, F | 95 | 99 | 122 |

[a]Linear low density polyethylene, 5-10 mil, 2-in./min., our experiments.
[b]Linear low density polyethylene, data from computer file.
[c]Copolymer of L-lactide/racemic D,L-lactide, Example 1.
[d]Heat deflection temperature.

The lactide polymerization can be stopped at incomplete monomer-to-polymer conversion in a controllable fashion. This is illustrated in Examples 1 and 2. The lactide monomer binds very intimately with polymers of lactides. Alternatively, the compositions can be derived by mixing of lactide with preformed polymer. In that case, the lactide added can be the same or different with respect to stereochemistry, i.e., L-, D-, or D,L-lactide to that used to make the polymer.

The compounding can be accomplished by blending the molten polymer with lactide monomer in conventional processing equipment such as a mill roll or a twin screw compounder. The normally stiff, glassy, lactide polymers are flexibilized by the lactide and remain transparent, colorless, and very nearly odorless. The lactide is not very fugitive, requiring heating, and a nitrogen sweep, typically, 170°-200° C. for 20-60 minutes to remove the lactide in a gravimetric analysis. Neither is the lactide visible in films under an optical microscope. The lactide domains are submicron in size. This flexibilizing of the poly(lactic acid) suggests its use as a environmentally biodegradable replacement for polyolefin, disposable, packaging films.

EXAMPLES 5-16

A series of experiments were performed in which copolymers of L- and racemic D,L-lactide were prepared, melt blended with variable amounts of lactide, and the physical properties of the blends evaluated as a function of the lactide composition. Monomer lactide content was assayed by a previously developed isothermal, thermogravimetric analysis. The lactide contents were measured before and after compounding and molding into films.

It was observed that open roll, 2 roll, milling tended to volatilize the lactide at temperatures required for the very high, molecular weight lactide copolymers. These losses could be minimized by masterbatching or by using lower molecular weight lactide copolymers (and their lower attendant mixing temperatures). A better mixing and blending method was a conventional, twin screw extruder, which minimized volatile losses. Some results are shown in Table 3.

Alternatively, a mixture of oligomeric lactic acid, or a derivative of an oligomer of lactic acid, oligomeric lactic acid and lactide can be used to prepare a flexible film, whereby the oligomers or their derivatives are added first, allowing the lactide to be mixed in the melt later at lower temperature. By adding oligomers first the melt viscosity decreases very significantly, allowing the temperature to be lowered, and the lactide can then be mixed in at a lower temperature without significant volatilization. This is demonstrated in Example 16A.

EXAMPLE 16A

A 90/10, L/D,L-lactide copolymer prepared by methods previously described, and analyzed by gel permeation chromatography to have a weight-average molecular weight of 480,000, a number average molecular weight of 208,000, was banded, that is, melted and mixed on an open 2-roll mill preheated to 350° F. The copolymer will not melt and band well on the mill below 350° F. To 25 grams of this melted copolymer was added 10 grams of oligomeric lactic acid of a degree of polymerization of 2.34. After all of the oligomeric lactic acid mixed in, the temperature was dropped to 300° F., where the mixing was still quite good. With the roll temperature at 300° F., 10 grams of L-lactide was added slowly and mixed. The mix was stripped from the roll and pressed into a thin film in a press at 300° F. The 5-10 mil thick film was colorless, transparent and very flexible. Without the lactide the resulting film would have been stiff. Without first adding the oligomeric lactic acid the lactide could not have been added on a mill without being lost to volatilization.

The blends of polylactide and lactide plasticizer are quite pliable, becoming increasingly so with increasing lactide content. They are colorless and transparent. Only a very faint (pleasant) odor of lactide is detectable and no discernable taste of lactide was noticeable. The Table 3 plasticized film samples were tear resistant, easily foldable, and can be punctured without shattering or tearing. They stiffen somewhat when placed in a cooler (5° C., 40° F.), but remain flexible and creasible without breaking. These films noticeably soften in the hand, indicating a glass transition temperature below 37° C. When the lactide content is less than 20 percent, the films will have a rattle typical of a polyolefin film. At greater lactide contents the films have the drape and "warm" feel of a plasticized poly(vinyl chloride) (PVC). In fact, the compositions of the invention are also a replacement for plasticized PVC in many applications.

Figure 2:
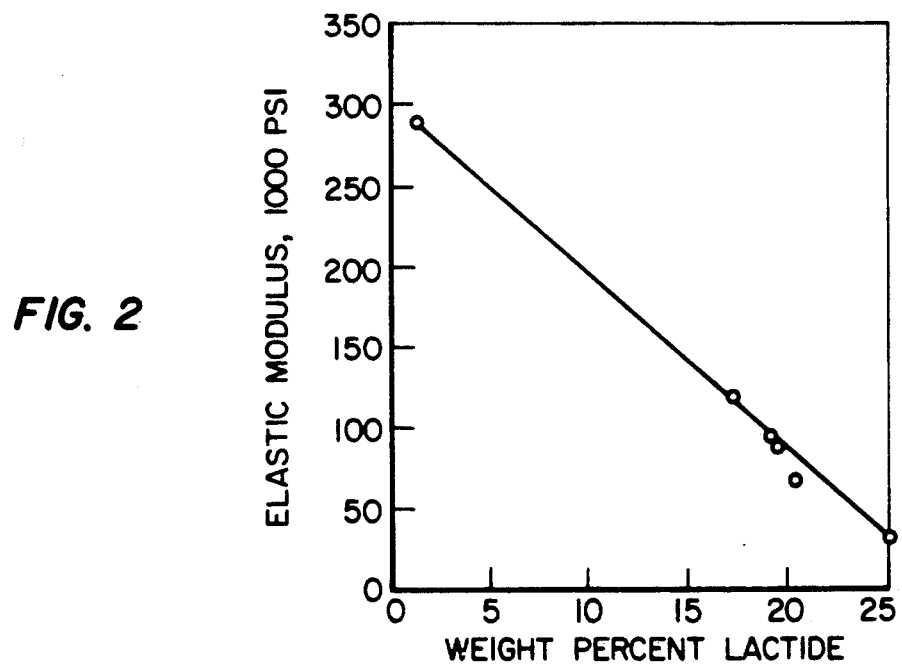
FIG. 2 is a graph showing the relationship between percent lactide in the composition as plasticizer and elastic modulus.

As shown in Table 3, the elastic moduli (initial tangent moduli) can be relatively high, similar to a linear low density polyethylene (LLDPE). This is an indication of potential form stability. Lower moduli and tensile strengths are similar to low density polyethylene (LDPE). Physical properties, as a function of lactide content, were plotted as shown in FIGS. 1 and 2. Referring to Table 3, at approximately 17-20 percent lactide content, the tensile properties are similar to polyethylenes used in trash bags and shopping bags.

At lower lactide contents, the blends have a similarity to polypropylene. Some data can be compared in Table 3. Table 4 defines the conventional plastics used in the comparisons.

TABLE 3

TENSILE PROPERTY COMPARISONS OF PLASTICIZED PLA[a]

| Ex. No. | Composition | Lactide % TGA | Elastic Modulus 1000 psi | 1% Secant Modulus 1000 psi | Yield Strength 1000 psi | Strain at Yield % | Break Strength 1000 psi | Strain at Break % |
|---|---|---|---|---|---|---|---|---|
| 5 | 90/10, L-/D,L-Lactide Copolymer | 1.3 | 289 | 291 | 0 | 0 | 7.5 | 3 |
| 6 | 90/10, L-/D,L-Lactide Copolymer | 17.3 | 119 | 119 | 2.23 | 4 | 2.29 | 288 |
| 7 | 90/10, L-/D,L-Lactide Copolymer | 19.2 | 95.5 | 90.3 | 1.97 | 5 | 4.24 | 536 |
| 8 | 90/10, L-/D,L-Lactide Copolymer | 19.6 | 88.7 | 88.7 | 1.72 | 4 | 2.12 | 288 |
| 9 | 90/10, L-/D,L-Lactide Copolymer | 20.5 | 50.3 | 50.3 | 1.21 | 5 | 2.16 | 338 |
| 10 | 90/10, L-/D,L-Lactide Copolymer | 25.5 | 33.7 | 22.9 | 0.32 | 4 | 2.44 | 546 |
| 11 | LPDE[b] | — | 41.3 | 40.6 | 1.51 | 17 | 1.60 | 365 |
| 12 | LLPDE[c] | — | 44.4 | 42.7 | 1.66 | 16 | 1.66 | 599 |
| 13 | Biaxially[d] oriented PE | — | 38.9 | 41.1 | 1.69 | 16 | 4.78 | 838 |
| 14 | Biaxially[e] oriented PE | — | 35.6 | 38.5 | 1.68 | 16 | 5.20 | 940 |
| 15 | HDPE[f] | — | 127.8 | 120.9 | 3.48 | 9 | 1.95 | 216 |

TABLE 3-continued

TENSILE PROPERTY COMPARISONS OF PLASTICIZED PLA[a]

| Ex. No. | Composition | Lactide % TGA | Elastic Modulus 1000 psi | 1% Secant Modulus 1000 psi | Yield Strength 1000 psi | Strain at Yield % | Break Strength 1000 psi | Strain at Break % |
| --- | --- | --- | --- | --- | --- | --- | --- | --- |
| 16 | PP[g] | — | 174 | 174 | 5.08 | 5 | 7.34 | 6 |

[a]ASTM 882; all samples were compression molded 5-10 mil films except Examples 13 and 14; strain rate 1.0 in/in min for all; D,L-lactide is racemic.
[b]USI low density polyethylene (petrothene No. 213).
[c]Exxon linear low density polyethylene (LLPE 6202,57).
[d]Machine direction.
[e]Cross machine direction.
[f]Phillips high density polyethylene (HMN 5060).
[g]Chisso polypropylene (XF 1932, melt index 0.52).

TABLE 4

MANUFACTURERS' DATA

| Supplier | Trade Name and/or Grade | Density, gm/cu cm | Recommended Melt Temperature, F. | Tensile Strength at Yield | Elastic Modulus in Flexure, $10^5$ psi | Melt Index gm/10 min |
| --- | --- | --- | --- | --- | --- | --- |
| LDPE (USI) | Petrothene | 0.924 | 360–550 | 1820 | 0.37 | 8.0 |
| LLDPE (Exxon) | 6202.57 | 0.926 | 425 | 1700 | 0.53 | 12.0 |
| HDPE (Phillips) | HMN 5060 | 0.950 | 425–525 | 3600 | 1.75 | 6.0 |
| 80% LLDPE (Exxon) 20% HDPE (Processing oil) | LPX 86 (Octene base) | 0.927 | 260 | — | — | 0.8 |
| Polypropylene (PP-Chisso) | XF1932 | 0.91 | 450–500 | 5872 | 3.05 | 0.52 |
| Polystyrene (Amoco) | RI | 1.05 | 400 | 7900 | 4.50 | 1.8 |

Table 3 reveals some data for lactide and polylactide mixtures. The results do not differ remarkably from similar compositions of Examples 1 and 2, prepared by other means. However, those skilled in the art will recognize that the precise physical properties will vary somewhat depending on the intimacy of the mixture, the tensile testing conditions, and the fabrication technique for preparing the films. Comparisons from Table 3 reveal that the lactide-polymer mixtures have a broad range of controllable compositions that mimic many conventional, nondegradable plastic types.

EXAMPLE 17

An oligomeric poly(lactic acid) (OPLA) was prepared for mixing with polylactides as follows. An 88 percent solution of L-lactic acid (956 g) was charged to a 3-neck flask (1 liter) fitted with a mechanical stirrer and a pot thermometer. The reaction mixture was concentrated under a nitrogen purge at 150°–190° C. at 200 mm Hg for 1 hour until the theoretical water of dilution was removed. No catalyst was used except for lactic acid and its oligomers. This temperature and vacuum were maintained and distillation continued for 2 hours until 73 percent of the theoretical water of dehydration was removed.

The total time required was 3 hours. At this time the reaction was stopped. The water samples and the pot oligomer were titrated with 0.5N NaOH. Some lactic acid, 26.2 g, was found in the water distillate. The pot oligomer (OPLA) was also refluxed with excess 0.5N NaOH, then back titrated with standard $H_2SO_4$. The data are recorded in Table 5. The oligomeric poly(lactic acid) flows well when hot, and shows some cold flow. It has a degree of polymerization of 3.4. It was used in Example 20 where it was melt blended with the polymer of Example 19.

TABLE 5

CHARACTERIZATION OF OPLA OF EXAMPLE 1

| Percent Dehydrated, Theoretical | Titratable Acid, percent | Titratable Ester, percent | Total Expressed as Lactic Acid percent | Degree of Polymerization |
| --- | --- | --- | --- | --- |
| 58 | 34.4 | 82.4 | 116.8 | 3.4 |

EXAMPLE 18

The procedure of Example 17 was repeated except the distillation was conducted more slowly. After 8 hours of heating during which the temperature was slowly advanced from 63° to 175° C. at 200 mm Hg, a sample of the pot was titrated to reveal 62.2 percent of theoretical water removal. Titration revealed a degree of polymerization of 4.3. The molecular weight of the oligomeric poly(lactic acid) was further advanced over 2 hours by heating at 179° C. and using a vacuum pump. The oligomeric poly(lactic acid) was no longer soluble in 0.1N NaOH, was water white, and would cold flow. This material is a second example of an oligomeric poly(lactic acid) preparation with somewhat higher degree of polymerization as compared to Example 1. It was mixed with polylactide in Examples 22 and 25. It is estimated that the degree of polymerization was about 6–10.

EXAMPLE 19

A polymer of lactide was prepared by methods similar to Example 3. A 90/10. weight percent L-/racemic D,L-lactide copolymer was melt polymerized using 0.02 parts per hundred, anhydrous stannous octoate catalyst. In a similar manner a 100 percent L-lactide homopolymer (L-PLA) was prepared. The copolymer was melt blended with the homopolymer at 350° F. in a twin-screw extruder at a weight ratio of 90/10, copolymer/homopolymer. Gel permeation chromatography of the blend reveals a weight-average molecular weight ($M_w$) of 182,000 and a number-average molecular weight ($M_n$) of 83,000. Residual lactide monomer by thermogravimetric analysis was 1.7 weight percent. This blend was mixed with the oligomeric poly(lactic acid) of Example 17 to provide material for Example 20. The tensile properties are listed in Table 6.

EXAMPLE 20

The polymer of Example 19 was melt blended with the oligomeric poly(lactic acid) of Example 17 on an open, 2-roll, mill for 20 minutes at 325° F. The mix was compression molded into films and tested as shown in Table 6. The gel permeation chromatography molecular weights were smooth, monomodal distributions ($M_w/M_n = 2.6$) with $M_w = 192,000$ and $M_n = 73,000$.

Figure 3:
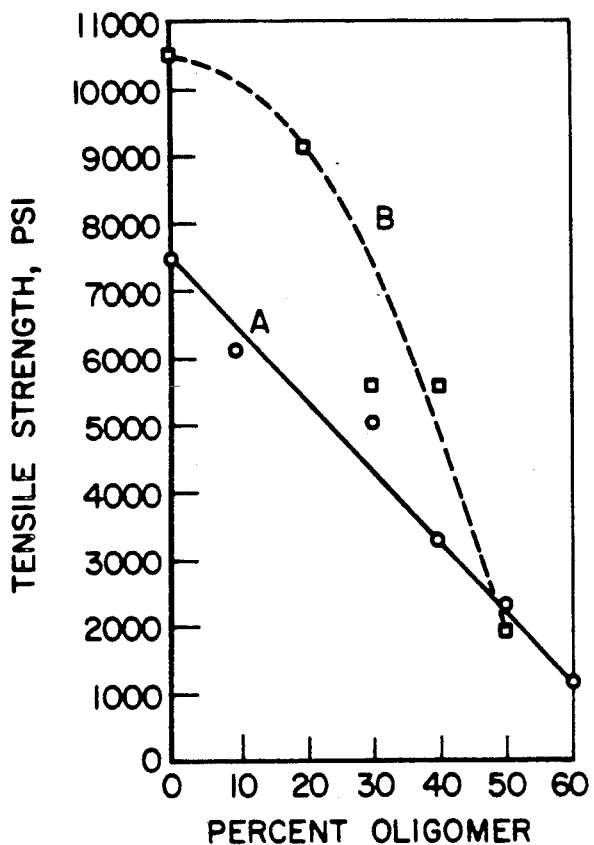
FIG. 3 is a graph showing the relationship between percent oligomer in the composition as plasticizer and tensile strength where curve A is for a 90/10 copolymer and curve B is for a 92.5/7.5 copolymer.
Figure 4:
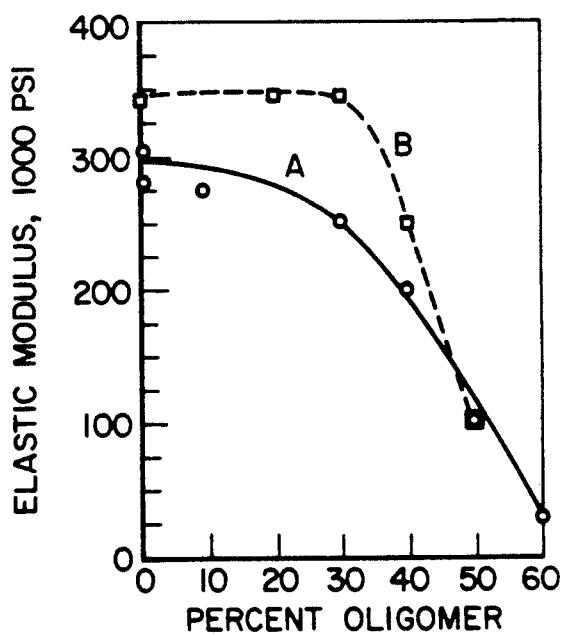
FIG. 4 is a graph showing the relationship between percent oligomer in the composition as plasticizer and the elastic modulus where curve A is for a 90/10 copolymer and curve B is for a 92.5/7.5 copolymer.

Table 7 lists the gel permeation chromatography molecular weights of these compositions. The tensile strengths and moduli are compared to the weight percentages of oligomeric poly(lactic acid) in FIGS. 3 and 4 (Lower Curves).

TABLE 7

MOLECULAR WEIGHTS AND GLASS TRANSITION TEMPERATURES OF 90/10 POLYLACTIDES AND OLIGOMERIC POLYLACTIC ACID

| Example Number | Composition, wt % | | Res.[a] Mon., % | GPC × 10$^{-3}$[b] | | | | Tg,[c] C |
|---|---|---|---|---|---|---|---|---|
| | Copolymer | Oligomer | | $M_n$ | $N_w$ | $M_z$ | $M_w/M_n$ | |
| 21 | 100[d] | 0 | 1.6 | 76 | 175 | 410 | 2.3 | 58 |
| 22 | 70[e] | 30[f] | 0.4 | 67[g] | 136 | 299 | 2.0 | 42 |
| 23 | 60[e] | 40[f] | 0.0 | 61[g] | 112 | 211 | 1.8 | 38 |
| 24 | 50[e] | 50[f] | 0.0 | 62[g] | 114 | 223 | 1.8 | 35 |
| 25 | 40[e] | 60[f] | 0.0 | 69[g] | 120 | 207 | 1.7 | 35 |

[a] Residual monomer by TGA.
[b] Molecular weight by GPC.
[c] Glass transition temperature by DSC.
[d] A blend of 90% of 90/10, L-/racemic D,L-lactide copolymer with 10% L-Pla.
[e] Example 21.
[f] Example 18.
[g] After blending; melt-blending on an open mill roll at 325 F.
All D,L-lactide is racemic, not meso.

EXAMPLES 26-30

A second series of copolymers was blended with the oligomeric poly(lactic acid). A 92.5/7.5, L-/racemic D, L-lactide copolymer was prepared by methods similar to Examples 19 and 21. This is Example 26 of Tables 8 and 9. It was melt blended with the oligomeric poly(lactic acid) of Example 18 on an open, 2-roll mill at 325° F. for approximately 20 minutes. The blends were compression molded into 3-5 mil thick films and their tensile properties and gel permeation chromatography molecular weights measured. The properties are recorded in Tables 8 and 9, and plotted in FIGS. 3 and 4. The second series of blends revealed significantly higher values for the tensile properties although the molecular weights were lower. This may be due to lower residual lactide monomer and/or the change in high polymer composition. All of the oligomeric poly(lactic acid) polylactide blends could be easily molded into tack free, transparent films.

TABLE 6

PROPERTIES OF MELT BLENDS OF 90/10 POLYLACTIDES AND OLIGOMERIC POLYLACTIC ACID

| Example Number | Composition, wt. % | | Lactide, %, TGA | Elastic Modulus, 1000 psi (a) | Break Strength, psi (a) | Strain at Break, % (a) | Tg, C (b) |
|---|---|---|---|---|---|---|---|
| | Polymer | Oligomer | | | | | |
| 19 | 100[c] | 0[d] | 1.7 | 298 | 7500 | 3 | 55 |
| 20 | 91[c] | 9[d] | 1.8 | 275 | 6113 | 2 | — |
| 21 | 100[e] | 0 | 1.6 | 308 | 7478 | 3 | 58 |
| 22 | 70[e] | 30[f] | 0.4 | 254 | 5052 | 3 | 42 |
| 23 | 60[e] | 40[f] | 0.0 | 202 | 3311 | 2 | 38 |
| 24 | 50[e] | 50[f] | 0.0 | 106 | 2334 | 25 | 35 |
| 25 | 40[e] | 60[f] | 0.0 | 36 | 1180 | 129 | 35 |

(a) ASTM 882; 5-10 mil, compression-molded films; strain rate 1.0 in./in./min.
(b) Glass transition temperature by differential scanning calorimetry.
[c] A blend of 90% of a 90/10, L-/D,L-lactide* copolymer with 10% poly(L-lactide), Example 19.
[d] Oligomeric PLA of Example 17.
[e] A blend of 80% of a 90/10, L-/D,L-lactide* copolymer with 20% poly(L-lactide).
[f] Oligomeric PLA of Example 18.
*racemic

EXAMPLE 21-25

The copolymer of Example 19 was melt blended with 20 percent of the L-PLA described in Example 19. The blend is listed as Example 21 in Table 6, where its analyses and tensile properties are listed. Example 21 was, in turn, melt blended with various amounts of the oligomeric poly(lactic acid) of Example 18 and these were tested as before and listed in Table 6, Examples 22 to 25.

TABLE 8
PROPERTIES OF MELT BLENDS OF 92.5/7.5 POLYLACTIDES AND OLIGOMERIC POLYLACTIC ACID

| Example Number | Composition, wt. % Polymer (c) | Composition, wt. % Oligomer (d) | Lactide, %, TGA | Elastic Modulus, 1000 psi, (a) | Break Strength, psi (a) | Strain at Break, % (a) | $T_g^{(b)}$ C |
|---|---|---|---|---|---|---|---|
| 26 | 100 | 0  | 0.2 | 338 | 10,527 | 4   | 61 |
| 27 | 80  | 20 | 0.3 | 346 | 9,144  | 4   | 52 |
| 28 | 70  | 30 | 0.2 | 346 | 5,675  | 2   | 46 |
| 29 | 60  | 40 | 0.6 | 249 | 5,617  | 3   | 36 |
| 30 | 50  | 50 | 1.5 | 112 | 1,984  | 119 | 36 |

(a) ASTM 882; 3-5 mil compression-molded films; strain rate 1.0 in./in./min.
(b) Glass transition temperature by differential scanning calorimetry.
(c) 92.5/7.5, L-/racemic D,L-lactide copolymer.
(d) Example 18.
All D,L-lactide is racemic, not meso.

TABLE 9
MOLECULAR WEIGHTS OF 9.25/7.5, L-/RACEMIC D,L-LACTIDE COPOLYMERS

| Example No. | OPLA % | $M_n$ | $M_w$ | $M_z$ | $M_w/M_n$ |
|---|---|---|---|---|---|
| 26 | 0  | 63 | 124 | 228 | 1.95 |
| 27 | 20 | 60 | 108 | 189 | 1.81 |
| 28 | 30 | 48 | 80  | 125 | 1.66 |
| 29 | 40 | 59 | 96  | 151 | 1.65 |
| 30 | 50 | 56 | 92  | 141 | 1.64 |

GPC × 10⁻³(a)

(a) Gel permeation chromatography (GPC) molecular weights as referred to monodisperse polystyrene standards.

EXAMPLES 31 AND 32

Film specimens with, and without plasticizer were exposed to seawater at Daytona, Fla. from March through May. The pH of the water varied from 7.3 to 7.6 and the salinity from 33.2 to 38.4 ppt. The water gradually warmed in the test from 15° to 27° C. The specimens were cut into strips and tensile tested before, and after, periodic intervals in the seawater. The results are shown in Table 10. All of the samples showed whitening and physical degradation, which became progressive with time. Without plasticizer the samples showed whitening and degradation after six weeks in the seawater. The oligomeric poly(lactic acid) polylactide blend degraded faster, revealing clear evidence of degradation after 3 weeks. The incorporation of 20 percent lactide provoked immediate whitening and obvious degradation after one week of exposure.

TABLE 10
PHYSICAL PROPERTIES AFTER SEAWATER EXPOSURE

| Example Number | Composition | Seawater Exposure Weeks | Tensile Properties, 1000 psi(a) Elastic Modulus | 1% Secant Modulus | Yield Strength | Break Strength | Strain, % Yield | Strain, % Break |
|---|---|---|---|---|---|---|---|---|
| 31 | 90/10 copolymer 5% L-PLA | 0 | 305 | 292 | — | 7.6 | — | 4.7 |
|    |   | 3(b) | 315 | 301 | — | 7.1 | — | 3.1 |
|    |   | 6(c) | 317 | 317 | — | 7.3 | — | 3.0 |
|    |   | 9(d) | 228 | 230 | — | 6.2 | — | 3.0 |
|    |   | 12(e) | 355 | 343 | — | 3.9 | — | 1.0 |
| 20 | 90/10 copolymer with 10% oligomer | 0 | 275 | 275 | — | 6.1 | — | 2.0 |
|    |   | 3(b) | 291 | 281 | — | 6.8 | — | 2.9 |
|    |   | 6(c) | 246 | 246 | — | 3.9 | — | 2.0 |
|    |   | 9(d) | 211 | 105 | 2.2 | 1.4 | 3 | 2.0 |
|    |   | 12(e) | 103 | 103 | — | 1.7 | — | 1.0 |
| 32 | 90/10 copolymer with 1% fumaric acid | 0 | 300 | 298 | — | 7.0 | — | 3.0 |
|    |   | 3(b) | 292 | 291 | — | 6.5 | — | 2.5 |
|    |   | 6(c) | 318 | 318 | — | 6.9 | — | 2.0 |
|    |   | 9(d) | 226 | 223 | — | 6.1 | — | 3.0 |
|    |   | 12(e) | 70 | 122 | — | 0.8 | — | 1.0 |
| 9  | 92.5/7.5 copolymer with 20% lactide | 1(e) | Too brittle to test | | | | | |

(a) 0.5 × 5 in. strips of film, 12-17 mil; strain rate 1 in./in./min.
(b) 15-21 C, saline seawater, regularly exchanged.
(c) 20-22 C, saline seawater, regularly exchanged.
(d) 22-23 C, saline seawater, regularly exchanged.
(e) 22-27 C, saline seawater, regularly exchanged.

EXAMPLE 33

Examples 33 to 51 teach the use of incorporating lactide in conjunction with quenching to obtain pliability and transparency. Alternatively, the polymers can be annealed to improve stability against heat distortion.

Poly L-(lactide) was prepared by methods previously described. Thus 300 g of triply recrystallized and thoroughly dried L-lactide was loaded into a clean, flame-dried, argon-cooled, 500 ml round-bottom flask. The flask was fitted with a rubber septum and inlet and outlet syringe needles that admitted a continuous argon purge. Stannous octoate solution was prepared by dissolving 20 g in 110 ml of toluene, previously dried over molecular sieves, then distilling 10 ml toluene in order to azeotropically dry the solution. The final concentration was 0.2 g/ml stannous octoate in toluene. A 0.3 ml quantity was injected through the septum onto the L-lactide. The flask and its contents were placed in a 150° C. oil bath, and when melted, swirled vigorously to obtain a homogeneous mix. The argon purge continued and a thermocouple was fitted through the septum into the melt. The melt was 143° C. The temperature of the oil bath was advanced to 200° C. and heating and light purge continued for 20 hours. The temperature of the melt advances to 170°-174° C. in the first two hours of heating. The final temperature was 170° C. After 20 hours of heating the flask was cooled in air to room temperature and the solid polymer was transparent.

Polymer was recovered by shocking the flask with dry ice to free it from the glass. The residual monomer was analyzed by thermogravimetric analysis and the molecular weights by gel permeation chromatography. Differential scanning calorimetry reveals a glass transition temperature ($T_g$) at 53° C. and two melting point endotherms with peaks at approximately 170° and 190° C. The gel permeation chromatography molecular weights: $M_n=129,000$; $M_w=268,000$; $M_z=462,000$; $M_w/M_n=2.08$. Residual monomer by thermogravimetric analysis was 2.3 percent, (Example 33, Table 11.) The experiment shows that L-lactide can be polymerized above, or near, its melting point and the products remain transparent and more amorphous.

EXAMPLE 34

By methods similar to Example 33, 104.0 g of L-lactide was polymerized using 0.10 ml of stannous octoate catalyst solution. However, the reaction temperatures were 155°-165° C. for 72 hours. The polymer (No. 34 of Table 11) slowly crystallizes upon forming and is a white opaque solid at reaction or room temperature. Since the sample was smaller than the preceding experiment the polymer cooled more quickly, but it did still not quench to a transparent solid. In comparison to Example 33, the lower reaction temperature permits the poly(L-lactide) to crystallize and become opaque, thus an intimate dispersion of plasticizer does not form.

The temperature is slowly advanced in many of these experiments to accommodate the polymerization exotherm. The reaction temperature must reach at least 170°-175° C. before there is substantial monomer-to-polymer conversion, otherwise the poly(L-lactide) crystallizes and is difficult to remelt.

In Examples 36-42 the polymerization of L-lactide was repeated varying the conditions to obtain poly(L-lactides) with different residual lactide contents and crystallinities. The results are shown in Table 11, where it is seen that pliability and toughness were obtained only when the product has been quenched from the melt, is transparent at room temperature, and contained approximately 10 percent or more residual lactide. It is believed that the L-lactide homopolymer must be polymerized in the melt, and quenched from the monomer-polymer melt temperatures, to a transparent material as evidence of its homogeneous and intimately plasticized properties. When the poly(L-lactide) crystallizes during polymerization because the polymerization temperature is well below the polymer's melting point, the residual monomer is no longer effective as a plasticizer. If the polymer crystallizes upon cooling to room temperature, it also loses its plasticization. Annealing at elevated temperatures will restore crystallinity to amorphous samples.

TABLE 11

POLYMERIZATION OF L-LACTIDE

| Ex. No. | Catalyst Amount pph | Temp C. | Time, hours | Polymer Appearance | Residual Monomer Percent | Sample Size g |
|---|---|---|---|---|---|---|
| 33 | 0.02 | 156-201[a] 150-174[b] | 20 | clear transparent, hard, glassy | 2.30 2.30 | 300 300 |
| 34 | 0.02 | 155-165[a] | 72 | crystalline, opaque, hard brittle | — | 104 |
| 35 | 0.005 | 120-200[a] 111-200[b] | 24 | crystalline, opaque, hard, brittle | — | 100 |
| 36 | 0.02 | 135-145[a] 135-152[b] | 22 | crystalline[d], | 1.1 | 500 |
| 37 | 0.02 | 117-185[a] 120-175[b,c] | 24 | crystalline opaque, hard, brittle | 1.74 | 100 |
| 38 | 0.02 | 160-170[a] | 8 | crystalline opaque, hard, brittle | 2.18 | 2,000 |
| 39 | 0.02 | 145[a] 137-144[b] | 15 | crystalline opaque, hard, brittle | 3.6 | 25 |
| 40 | 0.0553 | 190[a] 160-215[b] | 0.3 | clear, pliable tough, transparent | 10.1 | 25 |
| 41 | 0.0553 | 188-193[a] 147-200[b] | 0.28 | clear, transparent, pliable except at edge of polymerizate | 22.9 | 25 |
| 42 | 0.02 | 145[a] 150-133[b] | 2.75 | crystalline[d], opaque, hard brittle | 52.5 | 25 |

[a]Oil bath temperature.
[b]Polymer melt temperature.
[c]This polymer crystallized at 160-169° as the temperature was advanced and it did not remelt.
[d]Transparent at reaction temperature, crystallizes upon cooling.

This transparency and intimacy of association between polymer and monomer is also affected by the ratio of L/D,L-lactide. At approximately 95/5 ratio the copolymer easily quenches to a transparent solid. The 90/10 ratio, L/D,L-lactide copolymer quenches quite easily. The 100 percent L-lactide polymer quenches with difficulty from thick sections of the polymer to a transparent material. Some comparisons are shown by Examples 43-47 of Table 12. Thinner cross sections, i.e., films of the L-lactide polymer can be plasticized and quenched to pliable and transparent materials. The 80/20 copolymer quenches very easily to a transparent solid. The latter has only a trace of crystallinity as seen by differential scanning calorimetry.

TABLE 12

TRANSPARENCY OF LACTIDE POLYMERS

| Ex. No. | Lactide L/D,L- Ratio | Temp., C$^{(a)}$ | Time, hours | O/T$^{(b)}$ | GPC M$_w$ | Residual Monomer, percent |
|---|---|---|---|---|---|---|
| 43 | 95/5 | 145-160 | 67 | SO | 385,000 | 2.64 |
| 44 | 100 | 135-152 | 22 | O | 322,000 | 1.1 |
| 45 | 90/10 | 150-157 | 45 | T | 821,000 | 4.95 |
| 46 | 90/10 | 150-170 | 48 | T | 278,000 | 1.37 |
| 47 | 80/20 | 135-175$^{(c)}$ | 23 | T | — | — |

$^{(a)}$Melt temperature (polymerization temperature).
$^{(b)}$Opaqueness/Transparency (O/T) after air-cooling of polymerizates; opaque (O), slightly opaque (SO), transparent (T).
$^{(c)}$Slow-cooled for 1 hour.
All D,L-lactide is racemic.

All of the lactide polymers thermoform easily, that is, when heated by a radiant heater until soft, then sucked down on an intricate mold, they all form the pattern of the mold easily. However, the poly(L-lactide) becomes partially cloudy and hazy upon cooling. The 95/5, 90/10, and 80/20 copolymers are quite clear and transparent throughout their thermoforms.

EXAMPLE 48

The poly(L-lactide) from Example 33 was melted and mixed on an open 2-roll mill for 5 minutes at 375° F. (190° C.), then compression molded at 375° C. for 2 minutes, then air-quenched to room temperature in approximately 30 seconds. Both 7-and 20-mil thick films were prepared. Both were clear and transparent without trace of haze or opacity. Residual monomer in the film was 0.79 percent. The films are very stiff.

EXAMPLE 49

The experiment was repeated except that the milling was continued for 10 minutes instead of 5 minutes. The films were analyzed by thermogravimetric analysis again and found to have 0.38 percent lactide. The films were clear, transparent, and stiff.

EXAMPLE 50

The mill-rolled polymer was also compression molded into a ¼×178×1 inch plaque. This plaque required 5-10 minutes to cool in the press by turning on the cooling water to the press. The plaque was white, opaque, and crystalline except for the extreme edges, which were transparent.

The above Examples 48-50 teach the quenching of films of poly L-lactide to maintain transparency. When cooled more slowly, they crystallize and lose their transparency.

As D,L-lactide is introduced as a comonomer, quenching can be replaced by ordinary cooling to retain transparency. Spherulitic crystallinity can be introduced into these films by annealing and the 100 percent L-lactide polymer is the fastest to crystallize. Where transparency is not required the higher L-lactide polymers can be annealed to greatly improve their resistance to thermal distortion. Conversely, where transparency is required, such as in a polystyrene offset, great care must be taken to avoid this type of opaque crystallinity.

EXAMPLE 51

The poly(L-lactide) film samples were annealed on a hot plate at 240° F. (115° C.). The film turned hazy in approximately 1 minute and completely cloudy in approximately 2 minutes. By way of comparison, a 90/10, L/D,L-lactide copolymer film required 10 minutes to turn hazy, 15 minutes to become completely cloudy. When suspended by one end horizontally in an oven and advancing the temperature slowly, the annealed poly(L-lactide) sample remained straight until a temperature of 295° F. (146° C.) was obtained. The film then bent over. The annealed 90/10 copolymer bent over at a temperature of 185° F. (85° C.). The results show that the amount of crystallinity of polylactides can increase their form-stability at elevated temperatures to a temperature that is well above their $T_g$.

EXAMPLES 52-55

The following examples illustrate the beneficial effects of adding lactide during compounding. The examples show that without lactide as modifier, the lactide polymer degrades during compounding. With the addition of lactide both discoloration and molecular weight decrease are prevented or substantially reduced during compounding.

Thus, in Example 52, a 90/10, L-/D,L-lactide copolymer prepared as described by previous methods using 0.02 pph SnCl$_2$.2H$_2$O catalyst was ground and extruded into pellets from a twin screw compounder, adding 5 weight percent lactide. The melt zone temperature of the extruder rose to 390° F., the polymer discolored, and the weight average molecular weight (M$_w$, by gel permeation chromatography) decreased by approximately 40 percent. The results indicated that insufficient lactide was added for this very high M$_w$ copolymer. The results are shown in Table 13. The pellets from this compounding were recompounded adding a further 10 weight percent lactide (Example 54). The melt zone temperature was 375° F., and the results were much better: further discoloration did not occur, molecular weight decreased slightly, or within experimental error, and a pliable composition was obtained.

TABLE 13

EFFECT OF LACTIDE AS MODIFIER DURING COMPOUNDING

| Ex. No. | Color | M$_w$$^{(a)}$ | M$_w$/M$_n$$^{(a)}$ | Lactide$^{(b)}$ weight percent |
|---|---|---|---|---|
| | Before Compounding | | | |
| 52 | light yellow | 513 | 2.15 | 0.78 |

TABLE 13-continued

EFFECT OF LACTIDE AS MODIFIER DURING COMPOUNDING

| Ex. No. | Color | $M_w{}^{(a)}$ | $M_w/M_n{}^{(a)}$ | Lactide$^{(b)}$ weight percent |
|---|---|---|---|---|
| 53 | light yellow | 278 | 1.80 | 1.37 |
| After Compounding | | | | |
| 52 | dark yellow | 322 | 2.05 | 5.56$^{(c)}$ |
| 53 | yellow | 184 | 1.90 | 2.26 |
| 54 | dark yellow | 307 | 2.00 | 14.4$^{(d)}$ |
| 55 | colorless$^{(e)}$ | 324 | 1.99 | 14.6 |

$^{(a)}$GPC × 10$^{-3}$.
$^{(b)}$By thermogravimetric analysis, at 200 C.
$^{(c)}$Five weight percent lactide added during compounding.
$^{(d)}$Further 10 weight percent lactide added during compound.
$^{(e)}$Thin film.

To ascertain that the second compounding and extrusion were facilitated due to the lactide modifier and not the decreased molecular weight, another compounding (Example 53) was performed starting with a similar-$M_w$ copolymer of 90/10, L-/D,L-lactide. In this case, no lactide was added back in during the compounding. The melt zone temperature was 382° F., the copolymer was discolored, and the $M_w$ decreased by approximately 66 percent. In addition, approximately 5 percent more torque was required to compound the mix of $M_w$ 278,000 as compared to the one of $M_w$ of 322,000 with added lactide.

After compounding twice with lactide, Example 54 was analyzed by thermogravimetric analysis and found to have a lactide content of 14.4 percent. The material of Example 54 was converted to a blown film by means of a Haake-Brabender extruder in Example 55. Thin films of this composition are colorless, highly transparent, and very pliable and extensible as described below in Examples 60–64. The Mw by gel permeation chromatography was 324,000 (cf. Mw=307,000 before compounding and extrusion). The Tg of this plasticized material is 42° C. and differential scanning calorimetry reveals a very small amount of crystallinity melting at approximately 138° C. The amount of lactide present is 14.6 percent as estimated by thermogravimetric analysis.

EXAMPLES 56 AND 57

The compounded polylactides, Example 52 and 53, were mixed together in the twin-screw compounder with extra lactide to raise the lactide level to approximately 20 percent. The compounding temperature was 347° F. (175° C.), much reduced from the previous 375° to 385° F. The compounding proceeded smoothly without further discoloration.

The above results clearly show the beneficial effects of added lactide as modifier. The required torque to compound the compositions, the discoloration, and the working temperature are decreased when adding lactide. Further evidence of plasticization is seen in the lowered Tg and the pliability of the compositions. In addition, molecular weight decreases are avoided and stable compositions are obtained. It will be obvious to those skilled in the art that the amount of lactide employed depends on many factors, including the desired amount of plasticization sought, the type of compounder that is used, and the molecular weight of the polylactides.

EXAMPLES 58 AND 59

Examples 58 and 59 illustrate blown film extrusion of polylactides. These pliable films mimic polyolefins. The plasticized compounds of Examples 56 and 57 were adjusted to approximately 20 percent lactide in the twin-screw extruder. They were converted to blown films using a Haake-Brabender extruder. This consists of a ¾-inch extruder with a blown-film die and take-up device. The blown-film was achieved using a 12.7 mm outside diameter orifice and a pin to establish an extrusion gap of 0.483 mm. An extrudate temperature of 187° C. was maintained. A stable bubble was blown at this temperature with the inflation air at 3 oz/in.$^2$ gauge pressure. Cooling air was blown against the exterior of the bubble at 18 psi. Since the final average film thickness was 0.158 mm (6.2 mil), the blow-up ratio was 3:1. When the extruder gap was reduced from 0.483 to 0.254 mm, or the temperature raised, the polymer quenched readily to a crystalline, cloudy extrudate that would not expand. The larger orifice die produced an extrudate that was thicker and more viscous, cooled more slowly, and expanded in a consistent manner. The extruded film exhibited some elastic memory when stretched. The film also was resistant to tear and puncture and was very difficult to break by stretching. The blown film had an average elastic modulus of 117,000 psi, an average tensile strength of 3,735 psi, and an average elongation to break of 370 percent. This modulus is slightly higher than that of linear low density polyethylene, but the strength and elongation to break are comparable. The Elmerdorf Tear Strength (ASTM 1922) was 424 g in the cross machine direction and 183 g in the machine direction. The Tg of the material was 36° C., $M_w$ by gel permeation chromatography was 229,000, the residual lactide by thermogravimetric analysis was 19.7 percent, and the differential scanning calorimetry curves showed a weak endotherm centered at approximately 135° C.

EXAMPLES 60 TO 64

These examples illustrate plasticization with oligomeric esters of poly(lactic acid). Copolymers of 90/10, L-/D,L-lactide were melt blended with added lactide, esters of oligomeric/lactic acid, and mixtures thereof. They were characterized by tensile and thermal properties.

In Example 60, a control copolymer of 90/10, L-/D,L-lactide was assayed by thermogravimetric analysis to be 6.74 percent lactide. This was mixed with 30 percent by weight oligomeric polymethyllactate (Mella) in Example 61, which was prepared by heating 2,500 g of (S)-methyllactate in an autoclave at 210° C. for 3 hours, then collecting the Mella which fractionally distilled at 81 to 85° C./1.25 torr. The mixture was melt blended on an open 2-roll mill at approximately 350° F. The blend was compression molded in a press at approximately 350° F. into clear, pliable films. The tensile properties, before and after, adding the Mella are recorded in Table 14. The glass transition temperature (Tg) was reduced by the Mella plasticizer.

For Example 62, the 90/10, L-/D,L-lactide copolymer was melt blended with added L-lactide in a twin screw extruder to adjust the L-lactide content to 20 percent by weight. The blend was further mixed with oligomeric polyethyllactate (Ella) (Example 63) and Mella (Example 64). The properties of these blends are also recorded in Table 14.

TABLE 14

CHARACTERISTICS OF POLYLACTIDES[a] PLASTICIZED WITH OLIGOMERIC ESTERS OF LACTIC ACID

| Ex. No. | Plasticizer | Elastic Modulus psi | Break Strength psi | Strain at Break, % | $T_g$[b] | $T_m$[c] |
|---|---|---|---|---|---|---|
| 60 | 6.74%[d] L-lactide | 370,000 | 6,903 | 2 | 51 | 141 |
| 61 | 6.74%[d] L-lactide and 30% Mella[e] | 154,000 | 2,012 | 100 | 30 | 141 |
| 62 | 20% L-lactide | 101,000 | 2,637 | 278 | — | — |
| 63 | 20% L-lactide | 7,316 | 2,561 | 339 | — | — |
| 64 | 20% L-lactide and 30% Mella[e] | 3,620 | 495 | 83 | — | — |

[a]90/10, L-/racemic D,L-lactide copolymer.
[b]Glass transition temperature.
[c]Melting point.
[d]Analyzed by thermogravimetric analysis.
[e]Methyllactate oligomer.
[f]Ethyllactate oligomer.

EXAMPLES 65 TO 81

Comparative Examples 65 to 81 were selected from the patent literature that presented conditions most likely to result in materials of the present invention. The materials produced in these patents were not completely characterized, thus experiments were needed to allow a more complete characterization of the examples and provide meaningful comparisons that would demonstrate that the materials of the present invention are indeed novel. With regard to the present invention, compositions were sought that had residual lactide or lactic acid contents of about 0.1 to about 60 weight percent and in addition may have the lactide or lactic acid intimately dispersed within the polymer. The results fall into obvious categories. Thus, products with number-average molecular weights, $M_n$, less than 10,800 do not have the physical properties required in the present invention. In fact films from these low $M_n$ compositions were too brittle to be handled for tensile measurements.

It is known from the teachings herein that lactic acid, lactide, or oligomers of lactide or lactic acid, or derivatives of lactic acid must be present to provide plasticization and some pliability. The lactide must be present in amounts greater than about 10 weight percent while the oligomers of lactic acid, oligomers of lactide and the derivatives of lactic acid must generally be present above about 40 percent to provide obvious plasticization and pliability to polylactides. However, any amount of plasticizer as taught herein when added to the composition will change properties and can be used to obtain specialty formulated compositions. Thus, if lactide is intimately dispersed and effectively mixed as plasticizer, the mix of lactide and polylactide is completely transparent. The heterogeneous domain size of the lactide is small enough, generally less than one micron, so that it will no longer scatter light, i.e., it is intimately dispersed. Conversely, white opaque samples are always hard because they have crystallized under the test conditions. Crystallization squeezes the lactide out of the polymer mass, resulting in hard stiff compositions that are a gross mixture of monomer and polymer. This is also obvious from differential scanning calorimetry (DCS). Monomeric lactide that has segregated reveals itself with a separate melting point at 95° to 100° C., whereas well-plasticized samples do not show a distinct monomer melting point.

One very important point is that the cited patents frequently specify L-lactide homopolymer ("100 percent L-" in Tables 15A and 15B). The homopolymer of L-lactide easily crystallizes because of its high melting point. At lower reaction temperatures, the homopolymer can retain appreciable quantities of monomer, but the composition freezes during polymerization. At higher reaction temperatures, the L-lactide polymerizes so quickly that it is very difficult to stop the polymerization with substantial monomer left in the product.

Inspecting the results listed in Table 15A and 15B reveals that the comparative examples obtain either products with low residual lactide or else the polymerizations did not work or worked so poorly that greater than 40 percent lactide was left at the end of the specified polymerizations. Thus, Examples 65, 66 (very similar also to the work of Schneider), 67, 69, 73, 74, and 75 obtain low residual lactide. The Examples 70, 71, 72, 76, 77, and 78 examples did not work well as written in the patent examples. The best known laboratory techniques were added to the procedures, described in the footnotes, on these examples, from a historical standpoint (monomer purity, for example) in an effort to make the procedures work, with indifferent success. In no examples were pliable products found. Either glassy, or hard, crystalline, opaque products were obtained. It should be noted that only those examples using tin compounds as catalysts appear to be acceptable for many packaging applications.

Figure 5:
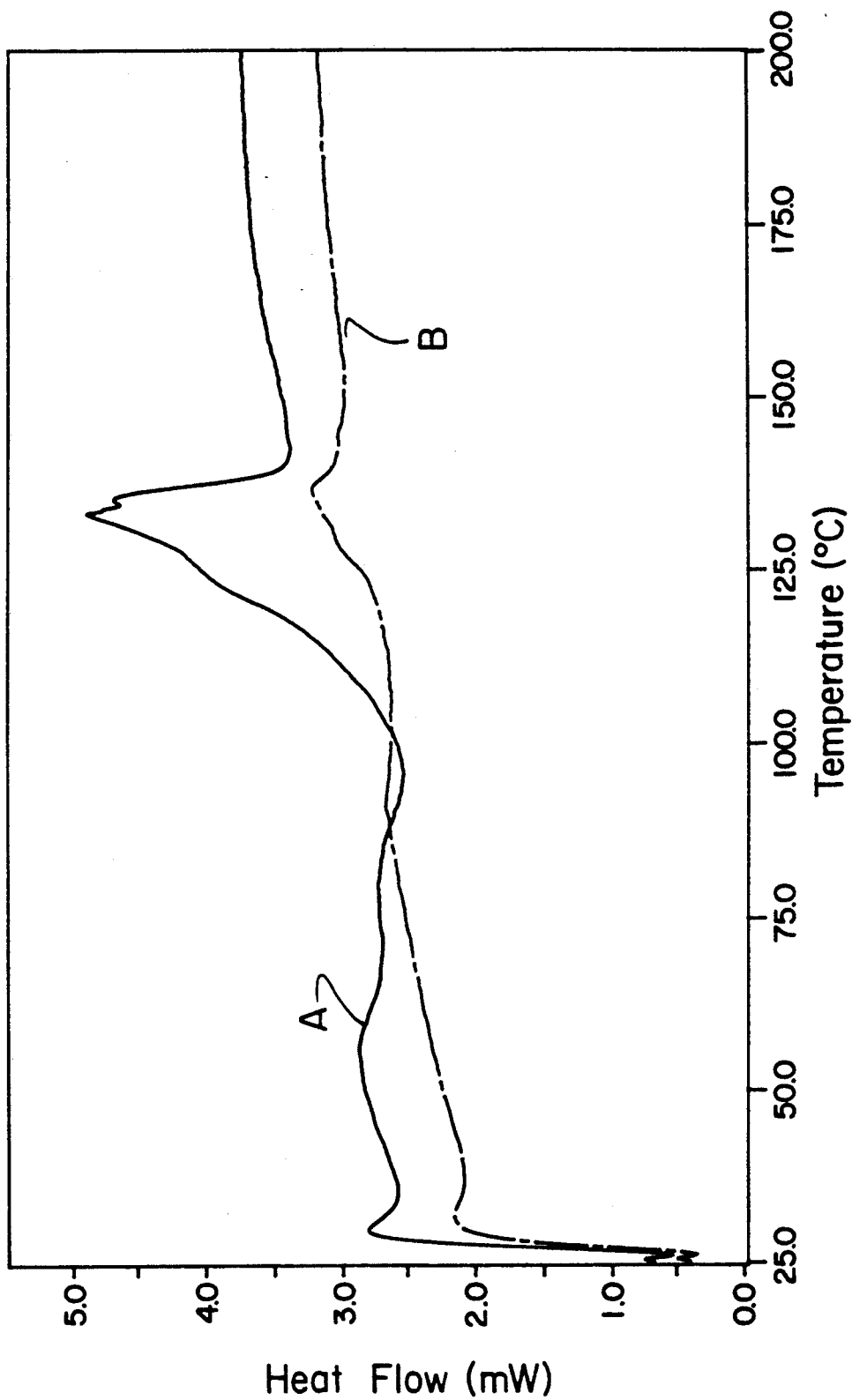
FIG. 5 is a graph showing a differential scanning calorimetry scan of a control composition prepared by the teachings of the present invention. Curve A represents a first scan of the material and curve B a second scan.

It appeared particularly that the Tunc methods would provide the materials of the present invention. To ascertain this, it was necessary to do the listed experiments on the teachings of Tunc in laborious detail as shown in Examples 79 to 81. FIG. 5 is a differential scanning calorimetry of one of the polylactides of the present invention. There is no detectable melting point for residual lactide monomer in the vicinity of 95° to 100° C. Only the polymer melting is seen. This material was analyzed separately by thermogravimetric analysis and shown to be 18.4 percent monomer lactide.

Figure 6:
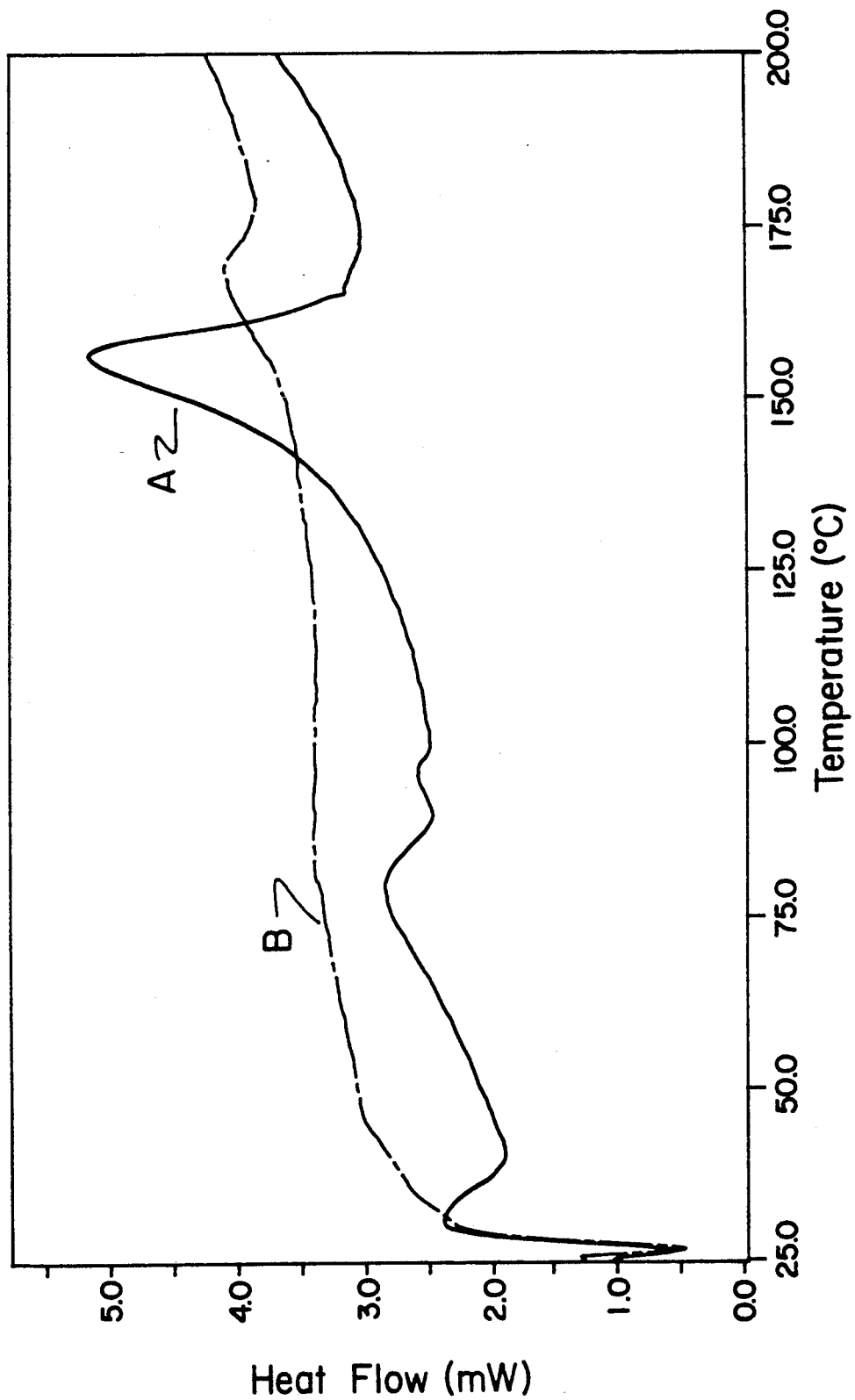
FIG. 6 is a graph showing a differential scanning calorimetry scan of the composition of Example 80. Curve A represents a first scan and curve B the second scan.

By way of contrast, preparations according to the exact replication of the Tunc methods were performed. Thermogravimetric analysis reveals 20.2 percent residual lactide for one such preparation. Example 80. The differential scanning calorimetry of this material is shown in FIG. 6, where a very distinct monomer melting point is seen. This corresponds to segregated lactide with a melting point within its own heterogeneous domain. Whereas this polymer is white, opaque, very hard and stiff, the composition of the present invention preparation is clear, transparent, and very pliable.

Figure 7:
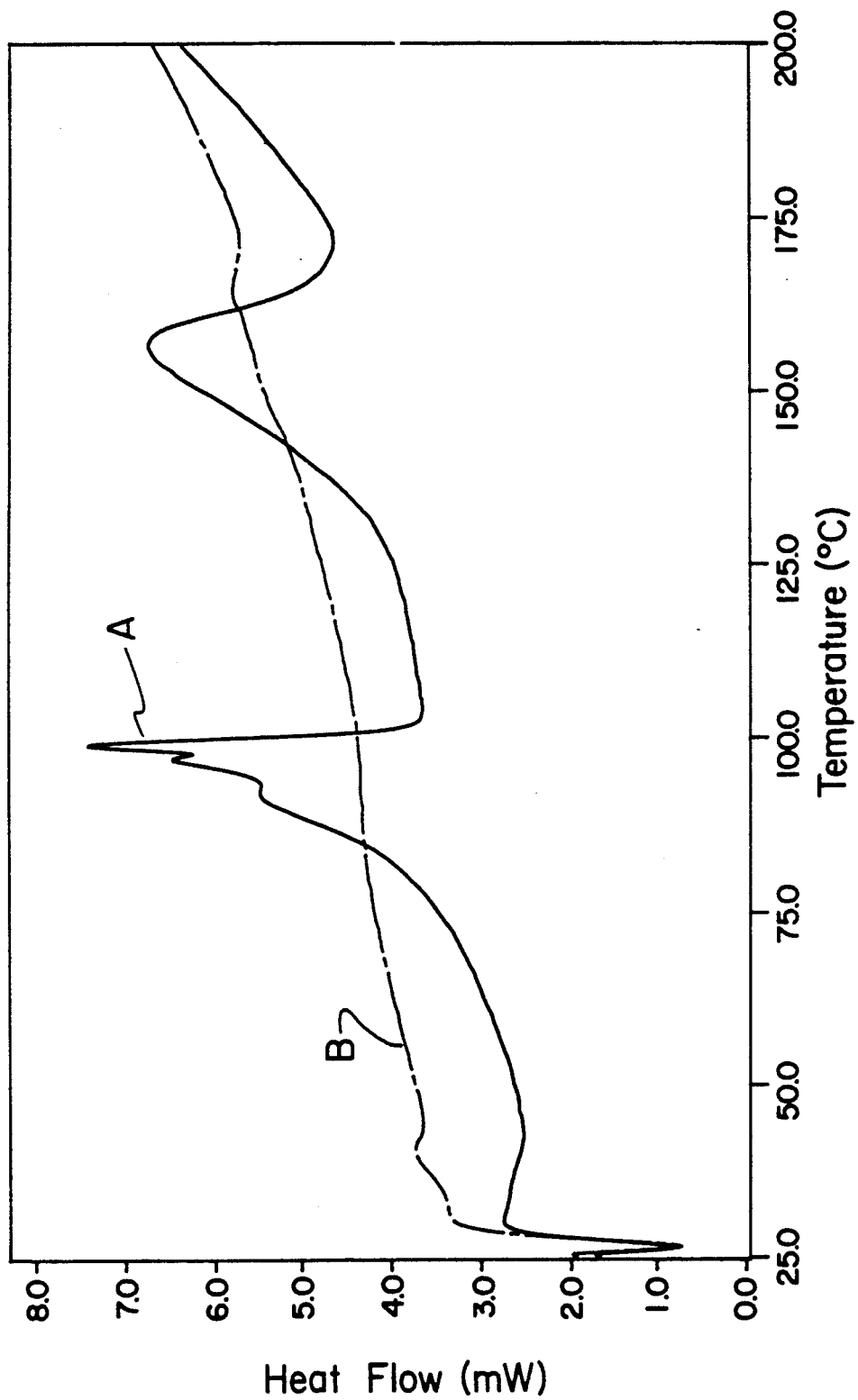
FIG. 7 is a graph showing a differential scanning calorimetry scan of the composition of Example 81. Curve A represents a first scan of the material and curve B the second scan.

A similar result was obtained repeating the teachings of Tunc in Example 81. This analyzed as 32.2 percent lactide and revealed a monomer melting point (FIG. 7).

The material was very white, crystalline, and hard. The results are reviewed in Table 15A and 15B.

TABLE 15A

RELATED ART POLYMERIZATIONS OF LACTIDE CONDITIONS

| Ex. No. | Patent | Pat. Ex. | Lactide Monomer(s) | Catalyst Type | pph | Polymerization Temp. C. | hours |
|---|---|---|---|---|---|---|---|
| 65 | 2,758,987 | 1 | L- | PbO | 0.30 | 150 | 42 |
| 66 | 2,758,987 | 3 | 50/50 L-/D,L | PbO | 3.00 | 150 | 89 |
| 67 | 3,982,543 | 3 | L- | PbO | 0.30 | 150 | 31 |
| 68 | DD 14548 | 2 | L- | SnO[a] | 0.009 | 193 | 3 |
| 69 | 4,137,921 | 4 | 90/10 L-/DL | Sn(Oct)$_2$, GA/dioxane[b] | 0.0553 | 180 190 210 | 0.33 0.33 0.33 |
| 70 | GB 755,447 | 4 | D,L | ZnO[c] | 0.02 | 150 | 24 |
| 71 | GB 755,447 | 2 | D,L | Zn Powder[d] | 0.02 | 140 | 25.5 |
| 72 | GB 755,447 | 6 | D,L | Zn Carbonate Hydroxide[c] | 0.02 | 140 150 | 2 3 |
| 73 | CA 932,382 | 1 | D,L | Tetraphenyl Tin | 0.02 | 165 | 20 |
| 74 | CA 923,245 | 1,7 & 8 | L- | Et$_2$Zn | 0.167 | 105–110 | 2 |
| 75 | DE 946,664 | 2 | D,L[e] | ZnCl$_2$ | 0.25 | 140 | 48 |
| 76 | DE 1,112,293 | 1 | L- | Sn Stearate | 0.0087 as Sn | 205–210 | 0.5 |
| 77 | 2,951,828 | 1 | L-[f] | SnCl$_4$ suspension[g] | 0.30 | 160 | 5 |
| 78 | 3,268,487 | 2 | D,L | Tris(2-chloroethyl) amine[h] | 0.88 | 80 | 24 |
| 79 | EP Applic. 108,635(1984) 4,550,449; 4,539,981 | 6, Polymer 8 | L- | Sn(Oct)$_2$ | 0.00108 | 165 | 93 |
| 80 | 4,539,981 & 4,550,449 | Polymer 33 | L- | Sn(Oct)$_2$ | 0.00119 | 136–139 | 64 |
| 81 | 4,539,981 & 4,550,449 | Polymer 37 | L- | Sn(Oct)$_2$ | 0.00324 | 115 | 64.5 |

[a]No reaction until recipe was changed by adding 0.75 pph of 88 percent lactic acid. Product was white, opaque, very hard and brittle; film too brittle to handle.
[b]Included was glycolic acid as chain transfer agent.
[c]Insoluble.
[d]Insoluble after 24 hours plus additional 1.5 hours with 700 μl 88 percent lactic acid and 100 μl H$_2$O.
[e]In toluene; product colorless and very viscous.
[f]In mineral spirits, Stoddard solvent No. R-66.
[g]Agglomerated.
[h]In dioxane containing 0.517 pph KOH; no polymerization.

TABLE 15B

RELATED ART POLYMERIZATIONS OF LACTIDE RESULTS

| Ex. No. | Residual Monomer, Percent | GPC × 10−3 $M_n$ | $M_w$ | $M_z$ | $M_w M_n$ | Polymerizate Appearance |
|---|---|---|---|---|---|---|
| 65 | 0 | 254 | 454 | 717 | 1.79 | Light yellow, crystalline, opaque |
| 66 | 0 | 97 | 187 | 322 | 1.94 | Light yellow, transparent |
| 67 | 0.85 | 95 | 195 | 325 | 2.06 | Partially opaque crystalline, partial transparent |
| 68 | 17.5(a) 7.1;7.7 | 5 7 | 7 8 | 9 10 | 1.47 1.25 | White, crystalline, opaque |
| 69 | 4.6 | 116 | 218 | 356 | 1.88 | Light yellow, transparent |
| 70 | 47.7 | — | — | — | — | White, crystalline (monomer), opaque |
| 71 | 65.3 | — | — | — | — | White, crystalline (monomer), opaque |
| 72 | 79.6 | — | — | — | — | White, crystalline (monomer), opaque |
| 73 | 1.4 | 116 | 214 | 340 | 1.84 | Yellow, transparent |
| 74 | 1.9 | 80 | 150 | 235 | 1.87 | Orange, crystalline, opaque |
| 75 | 5.4[i] 2.5;1.9[j] | 164 307 | 377 527 | 657 808 | 2.30 1.72 | Hard, colorless |
| 76 | 43.3 | 30 | 35 | 41 | 1.17 | Hard, crystalline, opaque |
| 77 | 8.6;9.6 | 219 | 343 | 504 | 1.57 | Hard, crystalline, opaque |
| 78 | 100 | — | — | — | — | All crystalline monomer |
| 79 | 5.0 film[k] | 14 14 | 26 26 | 35 35 | 1.88 1.82 | White, crystalline, opaque Some transparency at edges |
| 80 | 20.2[l] | greater than 1,000,000 | | | | White, crystalline opaque |

TABLE 15B-continued

RELATED ART POLYMERIZATIONS OF LACTIDE RESULTS

| Ex. No. | Residual Monomer, Percent | GPC × 10−3 | | | | Polymerizate Appearance |
|---|---|---|---|---|---|---|
| | | $M_n$ | $M_w$ | $M_z$ | $M_w M_n$ | |
| 81 | 32.2$^{(m)}$ | greater than 1,000,000 | | | | White, crystalline opaque |

$^{(i)}$Sample heated at 140 C, then 5 minutes in 60 C vacuum oven to remove solvent.
$^{(j)}$Sample heated overnight in 60 C vacuum oven to remove solvent.
$^{(k)}$Transparent, very stiff and brittle.
$^{(l)}$Tunc obtains 17.1 percent, very high molecular weight.
$^{(m)}$Tunc obtains 28.0 percent, very high molecular weight.

The above examples establish that an all-lactic acid composition can be a pliable thermoplastic useful for flexible, plastic packaging films and containers. By way of comparison, nonplasticized homopoly (L-lactide) is a highly crystalline polymer with a tensile strength of about 7000 psi with an elongation of 1 percent and an initial modulus of 500,000 psi. It is very brittle, opaque, and crazes easily. It is not a well behaved thermoplastic, nor is it transparent. Poly (racemic D,L-lactide) is an amorphous, glassy, polymer with a glass transition temperature of approximately 50° C., a tensile strength of about 6300 psi, an elongation of approximately 12 percent, and an initial modulus of 160,000 psi. It is also very brittle although transparent. In stark contrast, a copolymer of L-lactide/racemic D,L-lactide that is plasticized with lactide monomer is remarkably different. For example, the plasticized polymers can have a tensile strength of approximately 3900 psi, an elongation of 431 percent, and an initial modulus of 56,000 psi. The plasticized polymer is clear and colorless, and the blend must be heated to above 100° C. to remove the plasticizer.

Although theory would predict a more amorphous structure as a result of plasticization, what is surprising is the pliable, transparent, stable compositions that can arise, and, secondly, the nearly exact fit of properties needed for certain packaging applications, such as polyethylene. This invention comes at a time when there is a need for such initial properties in a material that is slowly environmentally biodegradable since it could alleviate plastic pollution problems.

It will be apparent to those skilled in the art that extremely intimate blends of high polymers and plasticizers are a rarity. Intimate plasticization allows a wide latitude in the initial physical properties and the time for environmental biodegradation.

The amount of plasticizer in the polymer depends on the compositional characteristics desired. If lactide is used as plasticizer the range is preferably 10 to 40 weight percent whereas if only oligomers of lactide or lactic acid are used the range may be from 10 to 60 weight percent. Surprisingly, oligomer may be added at up to 30 weight percent without substantially affecting the tensile strength or modulus. See FIGS. 3 and 4. Addition of 30 to 60 weight percent oligomers produces significant plasticization and attenuation of physical properties. This adds great economy to the composition since oligomeric lactic acid is cheaper than the high molecular weight polylactide. Oligomer may be prepared from lactic acid or any lactide. It is important to note that the oligomer of lactic acid normally contains significant amounts of lactic acid unless removed. This is an important consideration in tailoring compositions having specific properties. Those skilled in the art and knowing the teachings of this invention will be able to select reaction conditions to obtain appropriate chain lengths for the polymer, and the proportions of polymer and plasticizer so as to obtain fabricated compositions having physical properties similar to commonly used packaging thermoplastics and yet degrade comparatively rapidly. For example, higher amounts of plasticizer result in polymers having increased flexibility and increasingly tough physical properties, however, an increasing degradation rate will also be obtained. Further, shorter chain lengths for the polymer will require less plasticizer to obtain the same properties as with longer lengths.

Preferably polymerization of the monomers is at a temperature less than 129° C. Further processing of the plasticized polymer into a final product is preferably at a temperature sufficiently low to retain the plasticizer in the polymer. This temperature may be above 129° C. If additional monomer and/or oligomer are added after polymerization the retention of monomer during processing is of course not as critical.

The unoriented compositions of the invention should have a tensile strength of 300 to 20,000 psi, an elongation to failure of 50 to 1,000 percent and a tangent modulus of 20,000 to 250,000 psi. Preferably for a polyolefin replacement the compositions have a tensile strength of at least 3000 psi, an elongation to failure of at least 250 percent, and a tangent modulus of at least 50,000 psi.

A composition for the replacement of polyethylene is adjusted so that the unoriented composition has a tensile strength of about 1,200 to about 4,000 psi, an elongation to failure of about 100 to about 800 percent, and a tangent modulus of about 20,000 to about 75,000 psi, while a composition for the replacement polypropylene, is adjusted so that the unoriented composition has a tensile strength of about 4,500 to about 10,000 psi, an elongation to failure of about 100 to about 600 percent, a tangent modulus of about 165,000 to about 225,000 psi, and a melting point of about 150° to about 190° F.

The homopolymers and copolymers of the present invention are insoluble in water but upon constant contact with water are slowly degradable. However, degradation is fast when compared to polyolefin compositions that are replaced by the invention. Thus, throwaway objects made from the polymers are environmentally attractive in that they slowly degrade to harmless substances. If objects made from polymers of the invention are incinerated, they burn with a clean, blue flame.

The compositions herein are useful for replacement of polyolefin compositions and particularly polyethylene and polypropylene as well as polyvinyl chlorides and polyethylene terephthalate. In addition to the above list, the method is useful for replacement of polymers of styrene, vinyl acetate, alkyl methacrylate, alkyl acrylate. It is understood that copolymers made from mixtures of the monomers in the listed group and physical mixtures of the polymers and copolymers of the above group are likewise replaceable. Those skilled in the art will recognize that minor amounts of lactide and lactic acid can be replaced by contemplated equivalents such as glycolide, glycolic acid, and caprolactone.

While the invention has been described above with reference to various specific examples and embodiments, it will be understood that the invention is not limited to such illustrated examples and embodiments and may be variously practiced within the scope of the claims hereinafter made.

I claim:
1. A composition comprising:
   a. a poly(lactic acid), wherein the poly(lactic acid) has the repeating units,

$$\begin{array}{c} CH_3\ \ O \\ | \ \ \ \ \ \ \ || \\ \!+\!C\!\!-\!\!-\!\!-\!\!C\!\!-\!\!O\!\!\!+_{\!\!\overline{n}} \\ | \\ H \end{array}$$

wherein n is the number of repeating units and n is an integer, $150 \leq n \leq 20{,}000$; and
   b. a plasticizer selected from the group consisting of lactic acid, lactide, oligomers of lactic acid, oligomers of lactide, and mixtures thereof, wherein:
      1. the plasticizer is intimately dispersed within the polymer; and
      2. when lactic acid and/or lactide are selected they are present in an amount between about 10 and about 40 weight percent, and when oligomers are selected they are present in an amount between about 10 and about 60 weight percent.

2. The composition of claim 1, wherein the polymer is derived from monomer selected from the group consisting of L-lactide, D-lactide, meso D,L-lactide, racemic D,L-lactide, and mixtures thereof.

3. The composition of claim 2, wherein at least part of the plasticizer is selected from the group of lactides consisting of D-lactide, L-lactide, meso D,L-lactide, racemic D,L-lactide and mixtures thereof and at least one of the lactides is stereochemically different from the monomer used to prepare the polymer.

4. The composition of claim 1, wherein the oligomers of lactic acid, and the oligomers of lactide are defined by the formula:

$$\begin{array}{c} CH_3\ \ O \\ | \ \ \ \ \ \ \ || \\ HO\!\!+\!\!C\!\!-\!\!-\!\!-\!\!C\!\!-\!\!O\!\!\!+_{\!\!\overline{m}}\!\!H \\ | \\ H \end{array}$$

where m is an integer; $2 \leq m \leq 75$.

5. The composition of claim 4, wherein m is an integer: $2 \leq m \leq 10$.

6. The composition of claim 1, wherein the composition comprises plasticizer selected from the group consisting of lactic acid, D-lactide, L-lactide, meso D,L-lactide, racemic D,L-lactide, and mixtures thereof.

7. The composition of claim 1, wherein the composition is unoriented and has a tensile strength of about 300 to about 20,000 psi, an elongation to failure of about 50 to about 1,000 percent, and a tangent modulus of about 20,000 to about 250,000 psi.

8. The composition of claim 1, wherein the composition is unoriented and has a tensile strength of about 1,200 to about 4,000 psi, an elongation to failure of about 100 to about 800 percent, and a tangent modulus of about 20,000 to about 75,000 psi.

9. The composition of claim 1, wherein the composition is unoriented and has a tensile strength of about 4,500 to about 10,000 psi, an elongation to failure of about 100 to about 600 percent, a tangent modulus of about 165,000 to about 225,000 psi, and a melting point of about 150° F. to about 190° F.

10. A composition comprising:
    a. a poly(lactic acid), wherein the poly(lactic acid) has the repeating units, $$\begin{array}{c} CH_3\ \ O \\ | \ \ \ \ \ \ \ || \\ \!+\!C\!\!-\!\!-\!\!-\!\!C\!\!-\!\!O\!\!\!+_{\!\!\overline{n}} \\ | \\ H \end{array}$$

and wherein n is the number of repeating units and n is an integer, $150 \leq n \leq 20{,}000$; and
    b. a plasticizer of one or more oligomeric derivatives of lactic acid or oligomeric derivatives of lactide, selected from the group defined by the formula:

$$\begin{array}{c} CH_3\ \ O \\ | \ \ \ \ \ \ \ || \\ R'O\!\!+\!\!C\!\!-\!\!-\!\!-\!\!C\!\!-\!\!O\!\!\!+_{\!\!\overline{q}}R \\ | \\ H \end{array}$$

where R=H, alkyl, aryl, alkylaryl or acetyl, and R is saturated, where R'=H, alkyl, aryl, alkylaryl or acetyl, and R' is saturated, where R and R' cannot both be H, where q is an integer: $2 \leq q \leq 75$; and wherein the plasticizer is intimately dispersed within the polymer.

11. The composition of claim 9, wherein q is an integer: $2 \leq q \leq 10$.

12. The composition of claim 10, wherein the composition is unoriented and has a tensile strength of about 300 to about 20,000 psi, an elongation to failure of about 50 to about 1,000 percent, and a tangent modulus of about 20,000 to about 250,000 psi.

13. The composition of claim 10, wherein the composition is unoriented and has a tensile strength of about 1,200 to about 4,000 psi, an elongation to failure of about 100 to about 800 percent, and a tangent modulus of about 20,000 to about 75,000 psi.

14. The composition of claim 10, wherein the composition is unoriented and has a tensile strength of about 4,500 to about 10,000 psi, an elongation to failure of about 100 to about 600 percent, a tangent modulus of about 165,000 to about 225,000 psi, and a melting point of about 150° F. to about 190° F.

15. The composition of claim 10, wherein the polymer is derived from monomers of lactide selected from the group consisting of L-lactide, D-lactide, meso D,L-lactide, racemic D,L-lactide, and mixtures thereof.

16. The composition of claim 10, wherein the composition comprises from about 10 to about 60 weight percent plasticizer.

17. The composition of claim 10, comprising additional plasticizer dispersed within the composition that is selected from the group consisting of lactic acid, D-lactide, L-lactide, meso D,L-lactide, racemic D,L-lactide, oligomers of lactic acid, oligomers of lactide, and mixtures thereof.

18. The composition of claim 17, wherein the oligomers of lactic acid and the oligomers of lactide are defined by the formula:

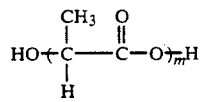

where m is an integer: $2 \leq m \leq 75$.

19. The composition of claim 18, wherein m is an integer: $2 \leq m \leq 10$.

20. A process for producing a composition comprising:
   a. polymerizing a lactide monomer selected from the group consisting of D-lactide, L-lactide, meso D,L-lactide, racemic D,L-lactide, and mixtures thereof, in the presence of a suitable catalyst;
   b. controlling the polymerization to allow the reaction to be stopped prior to complete polymerization;
   c. monitoring the level of remaining monomer;
   d. stopping the polymerization prior to complete reaction so that unreacted monomer in a predetermined amount is trapped in association with the polymer; and
   e. treating the polymer and unreacted monomer to obtain an intimately plasticized composition.

21. The process of claim 20, comprising stopping the polymerization reaction at an amount of remaining monomer between about 10 to about 40 weight percent.

22. The process of claim 20, comprising:
   f. incorporating additional plasticizer into the composition prior to or during the treating step wherein the plasticizer is selected from the group consisting of lactic acid, L-lactide, D-lactide, meso D,L-lactide, racemic D,L-lactide, oligomers of lactide, oligomers of lactic acid, and mixtures thereof.

23. The process of claim 20, comprising: incorporating additional plasticizer into the composition prior to or during the treating step, selected from the group consisting of oligomers of lactic acid, oligomers of lactide, and mixtures thereof, as defined by the formula:

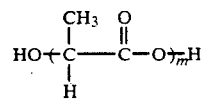

wherein m is an integer: $2 \leq m \leq 75$, and whereby the amount of oligomeric plasticizer is between about 10 and about 60 weight percent.

24. The process of claim 23, wherein m is an integer: $2 \leq m \leq 10$.

25. The process of claim 20, comprising: incorporating additional plasticizer into the composition prior to or during the treating step, selected from the group consisting of lactic acid, L-lactide, D-lactide, meso D,L-lactide, racemic D,L-lactide, and mixtures thereof, whereby the sum of unreacted monomer and additional plasticizer is between about 10 and about 40 weight percent.

26. The process of claim 20, comprising: incorporating additional plasticizer into the composition, prior to or during the treatment step, selected from one or more derivatives of an oligomer of lactic acid or an oligomer of lactide, defined by the formula:

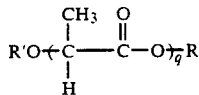

where R=H, alkyl, aryl, alkylaryl or acetyl, and R is saturated, where R'=H, alkyl, aryl, alkylaryl or acetyl, and R' is saturated, where R and R' cannot both be H, and where q is an integer: $2 \leq q \leq 75$.

27. The process of claim 26, wherein q is an integer: $2 \leq q \leq 10$.

28. The process of claim 26, comprising adding additional plasticizer selected from the group consisting of lactic acid, L-lactide, D-lactide, meso D,L-lactide, racemic D,L-lactide, oligomeric lactic acid, oligomeric lactide, and mixtures thereof.

29. The process of claim 20, comprising processing the intimately plasticized composition into a final product in a manner adapted to retain the plasticizer as an intimate dispersion in the polymer.

30. The process of claim 25, wherein the treatment step comprises quenching the polymer and unreacted monomer at a rate adapted to retain the monomer as an intimate dispersion within the polymer.

31. The process of claim 20, wherein the treatment step comprises melt fabricating, and quenching the polymer and unreacted monomer at a rate adapted to retain the monomer as an intimate dispersion within the polymer.

32. A process for producing a composition comprising:
   a. providing a poly(lactic acid);
   b. incorporating plasticizer into the poly(lactic acid) whereby the plasticizer is selected from the group consisting of lactic acid, D-lactide, L-lactide, meso D,L-lactide, racemic D,L-lactide, oligomers of lactic acid, oligomers of lactide, and mixtures thereof; and
   c. treating the obtained blend in a manner adapted to obtain an intimately plasticized composition.

33. The process of claim 32, wherein the incorporated plasticizer is selected from the group consisting of lactic acid, L-lactide, D-lactide, meso D,L-lactide, racemic D,L-lactide and mixtures thereof; and wherein the plasticizer is added to obtain a plasticizer content between about 10 to about 40 weight percent.

34. The process of claim 32, wherein the plasticizer is selected from the group consisting of oligomers of lactic acid, oligomers of lactide, and mixtures thereof; and wherein the plasticizer is added to obtain an oligomer content between about 10 to about 60 weight percent.

35. The process of claim 32, wherein the plasticizer is incorporated in a manner adapted to obtain an intimate dispersion of the plasticizer within the formed polymer.

36. The process of claim 35, comprising processing the composition into a final product in a manner adapted to retain the plasticizer as an intimate dispersion within the formed polymer.

37. The process of claim 35, comprising quenching the composition at a rate adapted to retain the monomer as an intimate dispersion within the formed polymer.

38. The process of claim 32, comprising melt fabricating and quenching the composition at a rate adapted to retain the monomer as an intimate dispersion within the polymer.

39. The process of claim 32, wherein the poly(lactic acid) is provided by polymerizing a lactide monomer selected from the group consisting of D-lactide, L-lactide, meso D,L-lactide, racemic D,L-lactide, and mixtures thereof in the presence of a suitable catalyst.

40. A process for producing a composition comprising:
   a. providing a poly(lactic acid);
   b. incorporating plasticizer into the poly(lactic acid) selected from one or more derivatives of an oligomer of lactic acid or an oligomer of lactide, defined by the formula:

$$R'O\!+\!\underset{\underset{H}{|}}{\overset{\overset{CH_3}{|}}{C}}\!\!-\!\!\overset{\overset{O}{\|}}{C}\!\!-\!\!O\!\!\underset{q}{\rangle}R$$

where R = H, alkyl, aryl, alkylaryl or acetyl, and R is saturated, where R' = H, alkyl, aryl, alkylaryl or acetyl, and R' is saturated, where R and R' cannot both be H, and where q is an integer: $2 \leq q \leq 75$; and
   c. treating the obtained blend in a manner adapted to obtain an intimately plasticized composition.

41. The process of claim 40, whereby q is an integer: $2 \leq q \leq 10$.

42. The process of claim 40, wherein the plasticizer is added in an amount to obtain a plasticizer content between about 10 to about 60 weight percent.

43. The process of claim 40, comprising incorporating additional plasticizer selected from the group consisting of lactic acid, L-lactide, D-lactide, meso D,L-lactide, racemic D,L-lactide, oligomers of lactic acid, oligomers of lactide, and mixtures thereof.

44. The process of claim 40, comprising incorporating the plasticizer in a manner adapted to obtain an intimate dispersion of the plasticizer within the polymer.

45. The process of claim 44, comprising processing the composition into a final product in a manner adapted to retain the plasticizer as an intimate dispersion within the polymer.

46. The process of claim 44, comprising quenching the composition at a rate adapted to retain the plasticizer as an intimate dispersion within the polymer.

47. The process of claim 40, comprising melt fabricating and quenching the composition at a rate adapted to retain the monomer as an intimate dispersion within the polymer.

48. The process of claim 40, wherein the poly(lactic acid) is provided by polymerizing a lactide monomer selected from the group consisting of D-lactide, L-lactide, meso D,L-lactide, racemic D,L-lactide, and mixtures thereof in the presence of a suitable catalyst.

49. A process for producing a blown film comprising:
   a. providing a poly(lactic acid);
   b. intimately mixing the poly(lactic acid) with plasticizer selected from the group consisting of lactic acid, L-lactide, D-lactide, meso D,L-lactide, racemic D,L-lactide, oligomers of lactic acid, oligomers of lactide, and mixtures thereof; whereby an intimate dispersion is obtained;
   c. extruding the plasticized poly(lactic acid) as a blown film while maintaining the intimate dispersion of plasticizer; and
   d. quenching the film in a manner adapted to obtain an intimately plasticized composition.

50. The process of claim 49, comprising: providing the poly(lactic acid) in step (a) having the repeating units, $$+\underset{\underset{H}{|}}{\overset{\overset{CH_3}{|}}{C}}\!\!-\!\!\overset{\overset{O}{\|}}{C}\!\!-\!\!O\!\!\underset{n}{\rangle}$$

wherein n is the number of repeating units and n is an integer, $150 \leq n \leq 20,000$; and plasticizing the poly(lactic acid) to obtain a composition which when unoriented has a tensile strength of about 1,200 to about 4,000 psi, an elongation to failure of about 100 to about 800 percent, and a tangent modulus of about 20,000 to about 75,000 psi.

51. The process of claim 49, comprising: providing the poly(lactic acid) in step (a) having the repeating units, $$+\underset{\underset{H}{|}}{\overset{\overset{CH_3}{|}}{C}}\!\!-\!\!\overset{\overset{O}{\|}}{C}\!\!-\!\!O\!\!\underset{n}{\rangle}$$

wherein n is the number of repeating units and n is an integer, $150 \leq n \leq 20,000$; and plasticizing the poly(lactic acid) to obtain a composition which when unoriented has a tensile strength of about 4,500 to about 10,000 psi, an elongation to failure of about 100 to about 600 percent, a tangent modulus of about 165,000 to about 225,000 psi, and a melting point of about 150° F. to about 190° F.

52. A process for producing a blown film comprising:
   a. providing a poly(lactic acid);
   b. intimately mixing the poly(lactic acid) with one or more derivatives of an oligomer of lactic acid or an oligomer of lactide, defined by the formula:

$$R'O\!+\!\underset{\underset{H}{|}}{\overset{\overset{CH_3}{|}}{C}}\!\!-\!\!\overset{\overset{O}{\|}}{C}\!\!-\!\!O\!\!\underset{q}{\rangle}R$$

where R = H, alkyl, aryl, alkylaryl or acetyl, and R is saturated, where R' = H, alkyl, aryl, alkylaryl or acetyl, and R' is saturated, where R and R' cannot both be H, and where q is an integer: $2 \leq q \leq 75$; whereby an intimate dispersion is obtained;
   c. extruding the plasticized poly(lactic acid) as a blown film while maintaining the intimate dispersion of plasticizer; and
   d. quenching the film in a manner adapted to obtain an intimately plasticized composition.

53. The process of claim 52, comprising: providing a poly(lactic acid) in step (a) having the repeating units, $$+\underset{\underset{H}{|}}{\overset{\overset{CH_3}{|}}{C}}\!\!-\!\!\overset{\overset{O}{\|}}{C}\!\!-\!\!O\!\!\underset{n}{\rangle}$$

wherein n is the number of repeating units and n is an integer, $150 \leq n \leq 20,00$; and plasticizing the poly(lactic acid) to obtain a composition which when unoriented has a tensile strength of about 1,200 to about 4,000 psi, an elongation to failure of about 100 to about 800 percent, and a tangent modulus of about 20,000 to about 75,000 psi.

54. The process of claim 52, comprising: providing the poly(lactic acid) in step (a) having the repeating units, $$\begin{array}{c} CH_3 \ O \\ | \ \ \ \ \ \| \\ -\!\!\!\left(C\!-\!\!-\!\!-\!\!C\!-\!O\right)_{\!\overline{n}} \\ | \\ H \end{array}$$

wherein n is the number of repeating units and n is an integer, $150 \leq n \leq 20{,}000$; and plasticizing the poly(lactic acid) to obtain a composition which when unoriented has a tensile strength of about 4,500 to about 10,000 psi, an elongation to failure of about 100 to about 600 percent, a tangent modulus of about 165,000 to about 225,000 psi, and a melting point of about 150° F. to about 190° F.

55. The process of claim 52, comprising adding a second plasticizer selected from the group consisting of lactic acid, L-lactide, D-lactide, meso D,L-lactide, racemic D,L-lactide, oligomers of lactic acid, oligomers of lactide, and mixtures thereof, and intimately mixing with the first intimate dispersion.

56. A process for incorporating plasticizer into poly(lactic acid) to obtain a blended composition comprising:
   a. melt blending with a poly(lactic acid), a first plasticizer selected from the group consisting of oligomers of lactic acid, oligomers of lactide, and mixtures thereof at a first temperature;
   b. melt blending with the obtained blend a second plasticizer selected from the group consisting of lactic acid, L-lactide, D-lactide, meso D,L-lactide, racemic D,L-lactide, and mixtures thereof, at a second temperature lower than the first temperature; and
   c. treating and quenching the second obtained blend in a manner adapted to obtain an intimately plasticized composition.

57. The process of claim 56, wherein the first plasticizer is defined by the formula:

$$\begin{array}{c} CH_3 \ O \\ | \ \ \ \ \ \| \\ HO\!\!\left(C\!-\!\!-\!\!-\!\!C\!-\!O\right)_{\!\overline{m}}\!H \\ | \\ H \end{array}$$

where m is an integer: $2 \leq m \leq 75$.

58. The composition of claim 57, wherein m is an integer: $2 \leq m \leq 10$.

59. The process of claim 56, comprising processing the composition into a final product in a manner adapted retain the plasticizer as an intimate dispersion in the polymer.

60. A process for incorporating plasticizer into poly(lactic acid) to obtain a blended composition comprising:
   a. melt blending with a poly(lactic acid), a first plasticizer selected from the group consisting of one or more derivatives of an oligomer of lactic acid or an oligomer of lactide, defined by the formula:

$$\begin{array}{c} CH_3 \ O \\ | \ \ \ \ \ \| \\ R'O\!\!\left(C\!-\!\!-\!\!-\!\!C\!-\!O\right)_{\!\overline{q}}\!R \\ | \\ H \end{array}$$

where R=H, alkyl, aryl, alkylaryl or acetyl, and R is saturated, where R'=H, alkyl, aryl, alkylaryl or acetyl, and R' is saturated, where R and R' cannot both be H, where q is an integer: $2 \leq q \leq 75$, at a first temperature;
   b. melt blending with the obtained blend a second plasticizer selected from the group consisting of lactic acid, L-lactide, D-lactide, meso D,L-lactide, racemic D,L-lactide, and mixtures thereof, at a second temperature lower than the first temperature; and
   c. treating and quenching the second obtained blend in a manner adapted to obtain an intimately plasticized composition.

61. The process of claim 60, wherein q is an integer: $2 \leq q \leq 10$.

62. The process of claim 60, comprising processing the composition into a final product in a manner adapted to retain the plasticizer as an intimate dispersion in the polymer.

63. The composition of claim 1, wherein the composition is an oriented film.

64. The composition of claim 63, wherein the oriented film composition is heat set.

65. The composition of claim 2, wherein additional minor amounts of other lactone monomers or glycolic acid are included.

66. The composition of claim 65, wherein the other lactone monomers included are glycolide and/or caprolactone.

67. The composition of claim 10, wherein the composition is an oriented film.

68. The composition of claim 67, wherein the oriented film composition is heat set.

69. The process of claim 20, wherein minor amounts of the selected monomers are replaced by other lactones.

70. The process of claim 69, wherein the minor amounts of lactones are glycolide and/or caprolactone.

71. The process of claim 20, comprising the additional steps of forming an intimately plasticized film and orienting the film above its $T_g$ but below its melting point.

72. The process of claim 71, comprising the additional step of heat setting the oriented film.

73. The process of claim 20, comprising modifying the properties by melt blending the composition with other polymers and copolymers of the lactides, glycolides, and caprolactones.

74. The composition produced by the process of claim 71.

75. The composition produced by the process of claim 72.

76. The process of claim 26, comprising the additional steps of forming an intimately plasticized film and orienting the film above its $T_g$ but below its melting point.

77. The process of claim 76, comprising the additional step of heat setting the oriented film.

78. The process of claim 26, comprising modifying the properties by melt blending the composition with other polymers and copolymers of the lactides, glycolides, and caprolactones.

79. The composition produced by the process of claim 76.

80. The composition produced by the process of claim 77.

81. The process of claim 32, comprising the additional steps of forming an intimately plasticized film and orienting the film above its $T_g$ but below its melting point.

82. The process of claim 81, comprising the additional step of heat setting the oriented film.

83. The process of claim 32, comprising modifying the properties by melt blending the composition with other polymers and copolymers of the lactides, glycolides, and caprolactones.

84. The composition produced by the process of claim 81.

85. The composition produced by the process of claim 82.

86. The process of claim 40, comprising the additional steps of forming an intimately plasticized film and orienting the film above its $T_g$ but below its melting point.

87. The process of claim 86, comprising the additional step of heat setting the oriented film.

88. The process of claim 40, comprising modifying the properties by melt blending the composition with other polymers and copolymers of the lactides, glycolides, and caprolactones.

89. The composition produced by the process of claim 86.

90. The composition produced by the process of claim 87.

91. The process of claim 49, comprising the additional step of orienting the film above its $T_g$ but below its melting point.

92. The process of claim 91, comprising the additional step of heat setting the oriented film.

93. The process of claim 79, comprising modifying the properties of the film by melt blending with other polymers and copolymers of the lactides, glycolides, and caprolactones.

94. The oriented film produced by the process of claim 91.

95. The oriented film produced by the process of claim 92.

96. The process of claim 52, comprising the additional step orienting the film above its $T_g$ but below its melting point.

97. The process of claim 96, comprising the additional step of heat setting the oriented film.

98. The process of claim 52, comprising modifying the properties of the film by melt blending with other polymers and copolymers of the lactides, glycolides, and caprolactones.

99. The oriented film produced by the process of claim 96.

100. The oriented film produced by the process of claim 97.

101. The process of claim 56, comprising the additional steps of forming an intimately plasticized film and orienting the film above its $T_g$ but below its melting point.

102. The process of claim 101, comprising the additional step of heat setting the oriented film.

103. The process of claim 56, comprising modifying the properties of the composition by melt blending with other polymers and copolymers of the lactides, glycolides, and caprolactones.

104. The composition produced by the process of claim 101.

105. The composition produced by the process of claim 102.

106. The process of claim 60, comprising the additional steps of forming an intimately plasticized film and orienting the film above its $T_g$ but below its melting point.

107. The process of claim 106, comprising the additional step of heat setting the oriented film.

108. The process of claim 60, comprising modifying the properties of the composition by melt blending with other polymers and copolymers of the lactides, glycolides, and caprolactones.

109. The composition produced by the process of claim 106.

110. The composition produced by the process of claim 107.

* * * * *

UNITED STATES PATENT AND TRADEMARK OFFICE
CERTIFICATE OF CORRECTION

PATENT NO.   : 5,180,765
DATED        : January 19, 1993
INVENTOR(S)  : Sinclair It is certified that error appears in the above-identified patent and that said Letters Patent is hereby corrected as shown below:

Column 1, line 1, in the title, delete "PACKAGING";
Column 1, line 1, in the title, delete "LACTIDES" and insert --POLYLACTIC ACID--.

Signed and Sealed this

Fourth Day of January, 1994

Attest:

BRUCE LEHMAN

*Attesting Officer*    *Commissioner of Patents and Trademarks*